United States Patent
Jegla (12)

(10) Patent No.: US 6,727,353 B2
(45) Date of Patent: Apr. 27, 2004

(54) NUCLEIC ACID ENCODING KV10.1, A VOLTAGE-GATED POTASSIUM CHANNEL FROM HUMAN BRAIN

(75) Inventor: Timothy James Jegla, Durham, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 09/833,466

(22) Filed: Apr. 11, 2001

(65) Prior Publication Data

US 2004/0053357 A1 Mar. 18, 2004

Related U.S. Application Data

(60) Provisional application No. 60/197,793, filed on Apr. 14, 2000.

(51) Int. Cl.[7] .......................... C12N 5/10; C12N 15/12; C12N 15/63; C07K 14/705
(52) U.S. Cl. ..................... 536/23.5; 435/69.1; 435/325; 435/71.1; 435/71.2; 435/252.3; 435/254.11; 435/471; 530/350
(58) Field of Search ............................... 536/23.1, 23.5; 530/350; 435/69.1, 325, 71.1, 71.2, 252.3, 254.11, 471

(56) References Cited

U.S. PATENT DOCUMENTS 5,710,019 A * 1/1998 Li et al. .................... 435/69.1

FOREIGN PATENT DOCUMENTS

| WO | WO 97/311112 A | 8/1991 |
| WO | WO 98/16185 A | 4/1998 |

OTHER PUBLICATIONS

Ottschytsch et al., "Obligatory heterotetramerization of three previously uncharacterized Kv channel alpha–subunits identified in the human genome", Proceedings of the National Academy of Sciences 99:12: 7986–7991 (2002).
Ottschytsch et al.,, Homo sapiens voltage–gated potassium channel Kv11.1 mRNA. complete CDS, EMBL Database accession No. AF348983, XP002232488.
de Miera et al., "Homo sapiens voltage–gated potassium channel subunit Kv10.1a mRNA, complete cds, alternatively spliced", EMBL Database accession No. AF454547, XP002232490.
de Miera et al., "Homo sapiens voltage–gated potassium channel subunit Kv10.1a mRNA, complete cds, alternatively spliced", EMBL Database accession No. AF454548, XP002232491.
Pongs, "Molecular Biology of Voltage–Dependent Potassium Channels", Physiological Reviews 72:4: S69–S88 (1992).
Pongs, "Structure–Function Studies on the Pore of Potassium Channels", Journal of Membrane Biology 136:1: 1–8 (1993).
Drewe et al., "Distinct Spatial and Temporal Expression Patterns of K+ Channel mRNAs from Different Subfamilies", Journal of Neuroscience 12:2: 538–548 (1992).
Pongs, "Potassium channel nomenclature: a personal view", Trends in Pharmacological Sciences 14:12: 435 (1993).
Waterson, "Homo sapiens chromosome 9 clone RP11–535E24, Working Draft Sequence, 7 unordered pieces", EMBL Database accession No. AC019222, XP002232489.

* cited by examiner

Primary Examiner—Prema Mertz
(74) Attorney, Agent, or Firm—Townsend and Townsend and Crew LLP

(57) ABSTRACT

The invention provides isolated nucleic acid and amino acid sequences of Slo potassium family members such as, antibodies to Kv10 subfamily members such as Kv10.1, methods of detecting Kv10, subfamily members such as Kv10.1, methods of screening for potassium channel activators and inhibitors using biologically active Kv10 subfamily members such as Kv10.1, and kits for screening for activators and inhibitors of voltage-gated potassium channels comprising Kv10 subfamily members such as Kv10.1.

5 Claims, 6 Drawing Sheets

```
1   MLKQSERRRSWSYRPWNTENEGSQHRRSICSIGARSGSQASIHGWTEGNYNYYIEEDED   kv10.1.PRC
1   MT----------------------------KHGSRSTSSLPP----------------   hKv2.1.PRC
1   MAE---------------------------KAPPGLNRKTSRSTLSLPP----------   hKv2.2.PRC

61  GEEEDQWKDDLAEEDQQAGEVTTAKPEGPSDPPALLSTLNVNVGGHSYQLDYCENAGFFK   kv10.1.PRC
15  --------------------EMEIVRSKACSRR--------VRINVGGIAHEVLWRTLDRLPR   hKv2.1.PRC
23  --------------------EVDIIRSKTCSRR--------VKINVGGINHEVLWRTLDRLPR   hKv2.2.PRC

121 TRLGRTATSTSRSRQLSICDDYEEQTEFYFFDRLPAVFQLVYNFYLSGVILVLDGICPRR   kv10.1.PRC
51  TRLGKLRDCNTHDSLLEVCDDYSLDDNEYFFDRHPGAFTSILNFYRTGRLHMMEEMCALS   hKv2.1.PRC
59  TRLGKLRDCNTHESLLEVCDDYNLNENEYFFDRHPGAFTSILNFYRTGKLHMMEEMCALS   hKv2.2.PRC

181 FLEELGWGVRLKTTPRCRICFEERRDELSERLKIQHELRAQAQVEEAEEIFDMRFYG    kv10.1.PRC
111 FSQELDYWGIDEIYLESCCQARYHQKKEQNNEELKREAETLREGEE--------R-DNTCCA hKv2.1.PRC
119 EGQELDYWGIDEIYLESCCQARYHQKKEQMNEELREAETMRDGEGEE-------E-DNTCCP hKv2.2.PRC

241 PQRRLWNLMEKPESSVAARAIGVASSTFVLVSVVALANTVEEMQHSGQEFFPDLRR     kv10.1.PRC
166 EKRKKLWDLLEKPNSSVAAKILAIISIMFIVLSTIALSLNTLPELQSLDEFGQSTDN----E hKv2.1.PRC
174 DKRKKLWDLLEKPNSSVAAKILAIVSILFIVLSTIALSLNTLPELQETDEFGQLNDN----R hKv2.2.PRC

301 INEHVEMLCMGEFTLEYLLRLASHPDLRRFARSAINLVDIMAILPLPLQLIECFTGEGH    kv10.1.PRC
224 QLAHVEAVCIAWFTMEYLLRFLSSPKKWKFFKGPLNAIDLLAILPYYVTIFLT-------   hKv2.1.PRC
232 QLAHVEAVCIAWFTMEYLLRFLSSNKWKFFKGPLNVIDLLAILPYYVTIFLT-------   hKv2.2.PRC

361 QRGQTVGSVGKVGQVLRVMRLMRIFRILKLARHSTGIRAFGFTLRQYQVGLLLFLAM    kv10.1.PRC
277 ESNKSVLQFQNVRRVVQIFRIMRILRILKLARHSTGLQSLGFTLRRSYNELGLLILFLAM   hKv2.1.PRC
285 ESNKSVLQFQNVRRVVQIFRIMRILRILKLARHSTGLQSLGFTLRRSYNELGLLILFLAM   hKv2.2.PRC
```

*FIG. 1A*

```
421  GIETFSAAVYSVEHDVPSINFTIIPRSWWWAAVSISTVGYGDMYPETHLGRFFAEICLAF  kv10.1.PRC
337  GIMIFSSLVFFAEKDEDTKFKFKSIPASFWWATITMTTVGYGDIYPKTLLGKIVGGLCCIA  hKv2.1.PRC
345  GIMIFSSLVFFAEKDEDAIKFKSIPASFWWATITMTTVGYGDIYPKTLLGKIVGGLCCIA  hKv2.2.PRC

481  GIILNGMPISILYNKFSDYMSKLRAYETTIRRE------RGEVNFHQ--RARKKIAEC    kv10.1.PRC
397  GVLVIALPIPIIVNNFSEFYKEQKRQEKAIKRREALERAKRNGSIVSHMKDAFARSIEM   hKv2.1.PRC
405  GVLVIALPIPIIVNNFSEFYKEQKRQEKAIKRREALERAKRNGSIVSHNLKDAFARSMEL  hKv2.2.PRC

532  LL------GSNPQLTPR-QEN                                        kv10.1.PRC
457  MDIVVEKNGENMGKKDKVQDNHLSENKWKTKRILSETSSKSFETKEQGSPEKARS---   hKv2.1.PRC
465  IDVAVEKAGESANTKDSADDNHLSESRWKARKALSETSSNKSFENKYQEVSQKDSHEQL  hKv2.2.PRC

546  ------                                                       kv10.1.PRC
514  -----SSSPQHLNVQQIEDMYNKMAKTQ--SQRILNTKESAAQSKP-KEELEMESIPSPVA  hKv2.1.PRC
525  NNTFSSSPQHLSAQKLEMLYNEITKTQPHSENPDCQEKPERPSAYEEIEMEEVVCPQE   hKv2.2.PRC

546  ------                                                       kv10.1.PRC
567  PIP-TRFEGVIDMRSMSSIDSFISCATDFPEATRFSHSPLTSLPSKTGGSTAPEVGWRGA  hKv2.1.PRC
585  QLAVAQTEVIVDMKSISSIDSFTSCATDFETETER-----SFLPPPSASHLQM------  hKv2.2.PRC

546  ------                                                       kv10.1.PRC
626  LGASGGRFVEANPSPDASQHSSFFIESPKSSMKTNNPLKLRALKVNFMEGDPSPLLPVLG  hKv2.1.PRC
632  ------KEPTDLPGTEEHQRAR---GPEFLTLSREKGPAARDGTLEYAPVDITVNLDASG  hKv2.2.PRC

546  ------                                                       kv10.1.PRC
686  M---YHDPIRNRGSAAAAVAGLECATILDKAVISPESSIYTTASAKTPPRSPEKHTAIAF  hKv2.1.PRC
683  SQCGLHSPLQSDNATDSPKSSLKGSNPLKSRSLKVNFKENRGSAPQTPPSTARPLPVTTA  hKv2.2.PRC
```

*FIG. 1B*

```
546     NFEAGVHQYIDADTDDEGQILYSVDSSPPKSLPGSTSPKFSTGTRSEKNHFESSPLPTSP            kv10.1.PRC
743     DESLTTPQHIST------ILI---EETESQGDRPCWALREQRLVEDL------EKGCPE            hKv2.1.PRC
743                                                                           hKv2.2.PRC

546     KFLRQNCIYSTEALTGKGPSGQEKCKIENHISPDVRVLPGGAHGSTRDQSI                     kv10.1.PRC
803     LQERGGASLK                                                             hKv2.1.PRC
787     GEPSRNCSLS                                                             hKv2.2.PRC
```

*FIG. 1C*

```
472  FFAALCIAFGIINGMPISILYNKFS    Kv10.1
439  VVALSSILSGILIMAFPVTSIFHTFS   Kv6.1
388  IVGGLCCIAGVLVIALPIPIIVNNES   Kv2.1
```

*FIG. 2.*

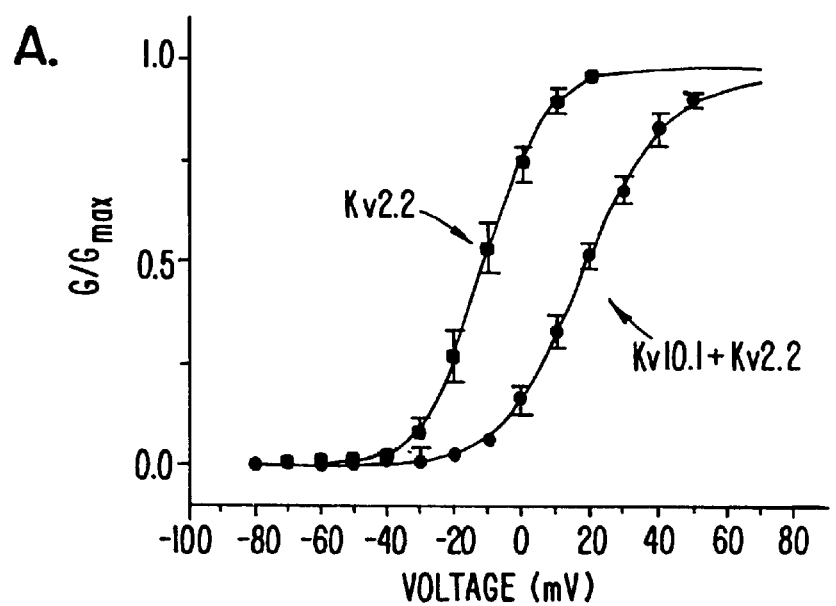
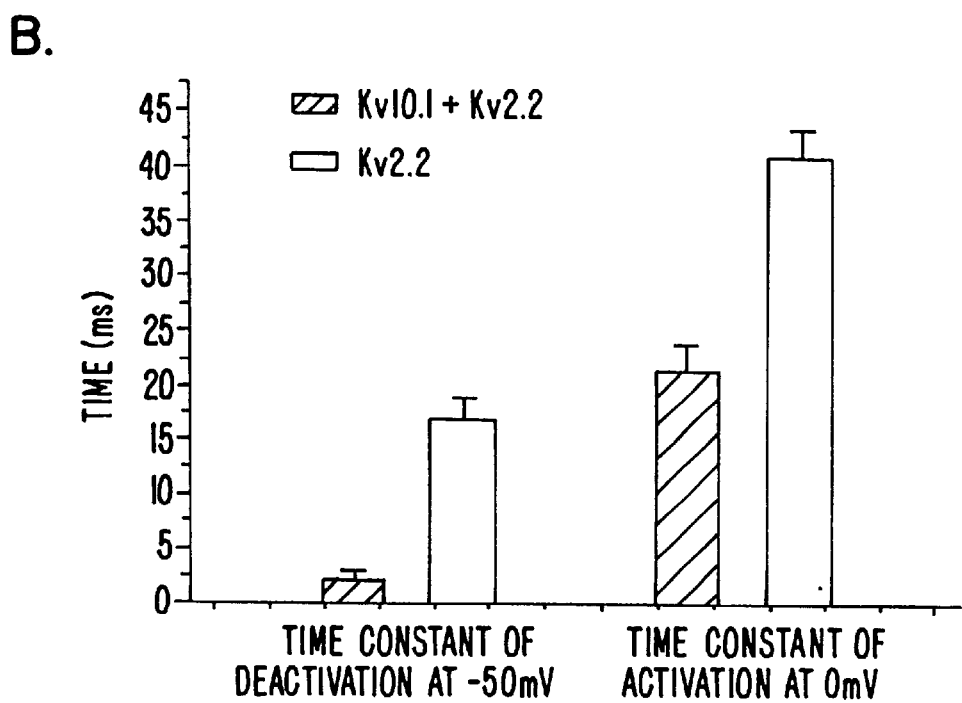
FIG. 4.

Kv10.1 mRNA

- WHOLE BRAIN — TR
- FETAL BRAIN — |
- TRIGEMINAL — |
- DRG — |
- FRONTAL CORTEX — TR
- HIPPOCAMPUS — |
- SPINAL CORD — +
- SUBSTANTIA NIGRA — +
- HYPOTHALAMUS — |
- CEREBELLUM — |
- KIDNEY — |
- HEART — |
- TESTIS — ++
- SPLEEN — |
- PANCREAS — |
- BLADDER — |
- PROSTATE — ++
- LIVER — |
- SKELETAL MUSCLE — |
- PLACENTA — |
- COLON — |
- RETINA — ++

TR = TRACE LEVELS

FIG. 5.

NUCLEIC ACID ENCODING KV10.1, A VOLTAGE-GATED POTASSIUM CHANNEL FROM HUMAN BRAIN

CROSS-REFERENCES TO RELATED APPLICATIONS

The present application claims priority to U.S. Ser. No. 60/197,793, filed Apr. 14, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35(7):805–829 (1997)). Three of these families (Kv, Eag-related, and KQT, now referred to as KCNQ) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels (also known as BK channels) have seven transmembrane domains (Meera et al., *Proc. Natl. Acad. Sci. U.S.A.* 94(25):14066–71 (1997)) and are gated by both voltage and calcium or pH (Schreiber et al.,*J. Biol. Chem.* 273:3509–16 (1998)). Another family, the inward rectifier potassium channels (Kir), belong to a structural family containing 2 transmembrane domains (see, e.g., Lagrutta et al., *Jpn. Heart. J.* 37:651–660 1996)), and an eighth functionally diverse family (TP, or "two-pore") contains 2 tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels have often been found to contain additional, structurally distinct auxiliary, or beta, subunits (e.g., Kv, Slo, and KCNQ potassium channel families). These beta subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KCNQ family beta subunit, minK, primarily changes activation kinetics (Sanguinetti et al., *Nature* 384:80–83 (1996)).

The Kv superfamily of voltage-gated potassium channels includes both heteromeric and homomeric channels that are typically composed of four subunits, as described above (see, e.g., Salinas et al., *J. Biol. Chem.* 272:8774–8780 (1997); Salinas et al., *J. Biol. Chem.* 272:24371–24379 (1997); Post et al., *FEBS Letts.* 399:177–182 (1996)). Voltage-gated potassium channels have been found in a wide variety of tissues and cell types and are involved in processes such as neuronal integration, cardiac pacemaking, muscle contraction, hormone section, cell volume regulation, lymphocyte differentiation, and cell proliferation (see, e.g., Salinas et al., *J. Biol. Chem.* 39:24371–24379 (1997)). Some alpha subunits of the Kv superfamily, of which the channels are composed, have been cloned and expressed, e.g., Kv2.1, Kv2.2, Kv5.1, Kv6.1 (Drewe et al., *J. Neurosci.* 12:538–548 (1992); Post et al., *FEBS Letts.* 399:177–182 (1996)); Kv8.1 (Hugnot et al., *EMBO J.* 15:3322–3331 (1996)); and Kv9.1 and 9.2 (Salinas et al., *J. Biol. Chem.* 39:24371–24379 (1997)). Expression patterns of some of these genes have also been examined (see, e.g., Verma-Kurvari et al., *Mol. Brain. Res.* 46:54–62 (1997); Maletic-Savatic et al., *J. Neurosci.* 15:3840–3851 (1995); Du et al., *Neurosci.* 84:37–48 (1998)).

SUMMARY OF THE INVENTION

The present invention therefore provides, for the first time, a new member of the Kv superfamily and the Kv10 family of potassium channels. A novel human DNA sequence, Kv10.1, encoding a voltage-gated potassium channel of the Kv (or KCNA) gene family was cloned and is presented herein. Kv10.1 defines the previously unidentified subfamily of Kv10 potassium channels, as it does not clearly fit into any previously defined subfamilies. Kv10.1 is expressed in the brain (e.g., whole brain, substantia nigra, and frontal cortex), spinal cord, prostate, and retina. Modulators of Kv10.1 are useful in treating CNS disorders, such as epilepsy and other seizure disorders, Parkinson's disease, migraines, psychotic disorders such as schizophrenia and depression, cognitive disorders such as learning and memory disorders, neuropathic pain, vision disorders, prostate hyperplasia, for controlling spermatocyte maturation and motility, for treating infertility, and as contraceptive agents. Modulators are also useful as neuroprotective agents (e.g., to prevent stroke).

In one aspect, the present invention provides an isolated nucleic acid encoding a polypeptide comprising an alpha subunit of a Kv10 potassium channel, the polypeptide: (i) forming, with at least one additional Kv alpha subunit, a Kv potassium channel having the characteristic of voltage-gating; and (ii) comprising a subsequence having at least 60% amino acid sequence identity to amino acids 102 to 514 of SEQ ID NO:3.

In one embodiment, the nucleic acid comprises a nucleotide sequence of SEQ ID NO:1 or SEQ ID NO:2. In another embodiment, the nucleic acid selectively hybridizes under moderately stringent hybridization conditions to a nucleotide sequence of SEQ ID NO:1 or SEQ ID NO:2. In another embodiment, the nucleic acid is amplified by primers that selectively hybridize under stringent hybridization conditions to the same template sequence as the primers selected from the group consisting of:

GCCATGCTCAAACAGAGTGAGAGGAGAC (SEQ ID NO:4)

GAGCGTGAAGAAGCCCATGCACAG (SEQ ID NO:5)

GCAGCACCCCGGACAGGTAGAAA (SEQ ID NO:6)

CGGCCGGGTCGCGGTCGAAGAAGT (SEQ ID NO:7)

CCACCATGAGGGCAGCCAACACCGCAGGAGCA (SEQ NO:8)

GGCTGTCTACTCTGTGGAGCACGAT (SEQ ID NO:9)

GAGTATTTCTAGAGGCAGTACTTTGTG (SEQ ID NO:10) and

ATTCTCTTGTCTTGGGGTGAGCTG (SEQ ID NO:11)

In another aspect, the present invention provides an isolated nucleic acid encoding a Kv10 polypeptide, the nucleic acid specifically hybridizing under stringent conditions to a nucleotide sequence of SEQ ID NO:1 or SEQ ID NO:2.

In another aspect, the present invention provides an isolated nucleic acid that specifically hybridizes under stringent conditions to a nucleic acid encoding an amino acid sequence of SEQ ID NO:3.

In another aspect, the present invention provides a method of detecting a nucleic acid, the method comprising contacting the nucleic acid with an isolated nucleic acid, as described above.

In another aspect, the present invention provides expression vectors comprising the nucleic acids of the invention, and host cells comprising such expression vectors.

In another aspect, the present invention provides an isolated polypeptide comprising an alpha subunit of a Kv10 potassium channel, the polypeptide: (i) forming, with at least one additional Kv alpha subunit, a Kv potassium channel having the characteristic of voltage-gating; and (ii) comprising a subsequence having at least 60% amino acid sequence identity to amino acids 102 to 514 of SEQ ID NO:3.

In one embodiment, the polypeptide specifically binds to antibodies generated against SEQ ID NO:3. In another embodiment, the polypeptide has a molecular weight of between about 58 kD to about 68 kD. In another embodiment, the polypeptide has an amino acid sequence of human Kv10.1. In another embodiment, the polypeptide has an amino acid sequence of SEQ ID NO:3.

In one embodiment, the polypeptide comprises an alpha subunit of a homomeric potassium channel. In another embodiment, the polypeptide encoded by the nucleic acid comprises an alpha subunit of a heteromeric potassium channel.

In another aspect, the present invention provides an antibody that specifically binds to the Kv10 polypeptide described herein.

In another aspect, the present invention provides a method for identifying a compound that increases or decreases ion flux through a Kv10 potassium channel, the method comprising the steps of: (i) contacting the compound with a Kv10 polypeptide, the polypeptide (a) forming, with at least one additional Kv alpha subunit, a Kv potassium channel having the characteristic of voltage-gating; and (b) comprising a subsequence having at least 60% amino acid sequence identity to amino acids 102 to 514 of SEQ ID NO:3; and (ii) determining the functional effect of the compound upon the potassium channel.

In one embodiment, the functional effect is a physical effect or a chemical effect. In another embodiment, the functional effect is determined by measuring ligand binding to the channel.

In one embodiment, the polypeptide is expressed in a eukaryotic host cell or cell membrane. In another embodiment, the functional effect is determined by measuring ion flux, changes in ion concentrations, changes in current or changes in voltage.

In one embodiment, the polypeptide is recombinant.

In another aspect, the present invention provides a method for identifying a compound that increases or decreases ion flux through a potassium channel comprising a Kv10 polypeptide, the method comprising the steps of: (i) entering into a computer system an amino acid sequence of at least 25 amino acids of a Kv10 polypeptide or at least 75 nucleotides of a nucleic acid encoding the Kv10 polypeptide, the Kv10 polypeptide comprising a subsequence having at least 60% amino acid sequence identity to amino acids 102 to 514 of SEQ ID NO:3; (ii) generating a three-dimensional structure of the polypeptide encoded by the amino acid sequence; (iii) generating a three-dimensional structure of the potassium channel comprising the Kv10 polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through a Kv potassium channel, the method comprising the step of contacting the Kv potassium channel, wherein the channel comprises a Kv10 alpha subunit, with an therapeutically effective amount of a compound identified using the methods described herein.

In another aspect, the present invention provides a method of detecting the presence of hKv10 nucleic acids and polypeptides in human tissue, the method comprising the steps of: (i) isolating a biological sample; (ii) contacting the biological sample with an hKv10-specific reagent that selectively associates with hKv10; and, (iii) detecting the level of hKv10-specific reagent that selectively associates with the sample.

In one embodiment, the human Kv10.1-specific reagent is selected from the group consisting of: human Kv10.1-specific antibodies, human Kv10.1-specific oligonucleotide primers, and human Kv10.1-nucleic acid probes.

In another aspect, the present invention provides, in a computer system, a method of screening for mutations of a human Kv10 gene, the method comprising the steps of: (i) entering into the computer a first nucleic acid sequence encoding a Kv10 polypeptide having a nucleotide sequence of SEQ ID NO:1 or SEQ ID NO:2, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In another aspect, the present invention provides, in a computer system, a method for identifying a three-dimensional structure of a Kv10 polypeptide, the method comprising the steps of: (i) entering into the computer system an amino acid sequence of at least 50 amino acids of the Kv10 polypeptide or at least 150 nucleotides of a nucleic acid encoding the polypeptide, the Kv10 polypeptide comprising a subsequence having at least 60% amino acid sequence identity to amino acids 102 to 514 of SEQ ID NO:3; and (ii) generating a three-dimensional structure of the polypeptide encoded by the amino acid sequence.

In one embodiment, the amino acid sequence is a primary structure and wherein said generating step includes the steps of: (i) forming a secondary structure from said primary structure using energy terms determined by the primary structure; and (ii) forming a tertiary structure from said secondary structure using energy terms determined by said secondary structure. In another embodiment, the generating step further includes the step of forming a quaternary structure from said tertiary structure using anisotropic terms encoded by the tertiary structure. In another embodiment, the method further comprises the step of identifying regions of the three-dimensional structure of the polypeptide that bind to ligands and using the regions to identify ligands that bind to a potassium channel comprising a Kv10.1 polypeptide.

BRIEF DESCRIPTION OF THE DRAWINGS

FIGS. 1A, 1B and 1C provide an amino acid alignment of Kv10.1 (SEQ ID NO:3) with Kv2.1 (SEQ ID NO:12) and Kv2.2 (SEQ ID NO:13). Identical amino acids are shaded, and amino acid position is given at the left margin. Gaps in the alignment are indicated by dashes.

FIG. 2: FIG. 2 provides an amino acid alignment of the S6 domains of Kv10.1 (SEQ ID NO:14), Kv6.1 (SEQ ID NO:15) and Kv2.1 (SEQ ID NO:16). Arrows mark two residues that typically differ between normal Kv family polypeptides that form functional channels as homomultimers and electrically silent Kv channel polypeptides that form functional channels as heteromultimers. These residues are always glycine (G) and proline (P), respectively, in Kv subunits that express as homotetramers. Kv10.1 differs at these residues, much like the electrically silent subunit Kv6.1.

FIG. 4. (A) Conductance vs. voltage relationships for oocytes expressing either Kv2.2 or both Kv2.2 and Kv10.1. Error bars show standard error and the smooth curves represent Boltzmann fits of the data, from which the voltage-dependent parameters given below are derived. Note that Kv10.1 causes both a decrease in the slope of the curve and a dramatic depolarized shift. The $V_{50}$ (point at which ½ of the full conductance is reached) for Kv2.2 is −6.9±1.7 mV. In contrast the $V_{50}$ obtained for Kv2.2–Kv10.1 currents is shifted over 25 mV to +19.0±2.0 mV. (B) Kv2.2 homomultimers and Kv2.2–Kv10.1 heteromultimers can be distinguished on the basis of activation and deactivation kinetics. Activation and deactivation time constants are given for both currents at 0 mV and −50 mV, respectively. Error bars indicate standard error. Kv10.1 causes a dramatic increase in the rate of deactivation, and also cause a roughly 2-fold increase in the rate of activation.

FIG. 5. mRNA Expression of Kv10.1 in select human tissues. Kv10.1 expression was assayed using RT-PCR as described in Example 3. Positive expression is indicated by plus signs (+++=very high, ++=high, +=moderate, tr=trace, low) and absence of expression is indicated by a dash.

DETAILED DESCRIPTION OF THE INVENTION

Figure 3:
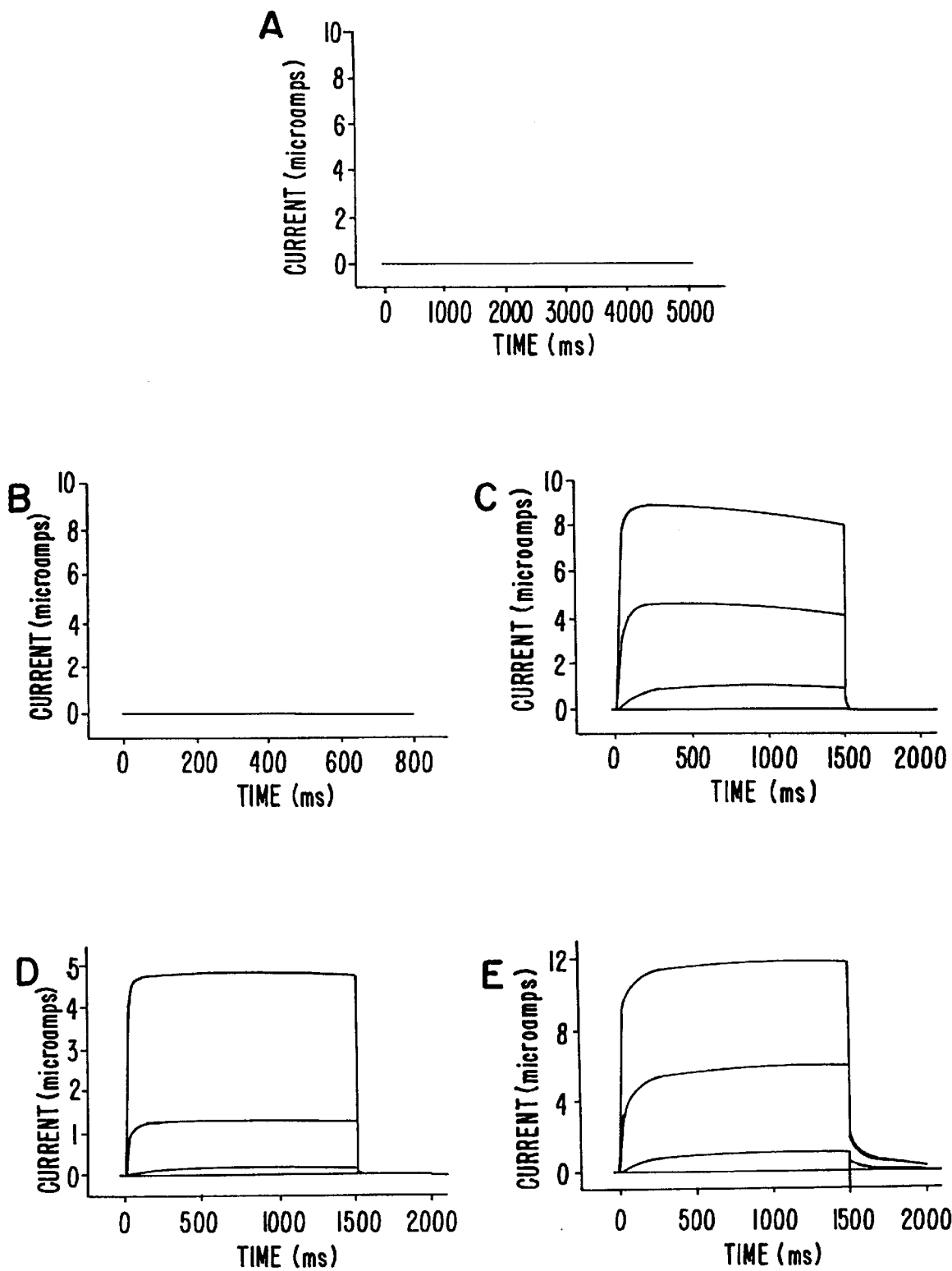
FIG. 3. Expression of Kv10.1 in Xenopus oocytes. All windows show families of current recorded under voltage clamp. The holding potential used was −90 mV and steps from −60 mV to +20 mV are shown in 20 mV increments. Tail currents were measured at −60 mV in (A)–(C), and −40 mV in (D) and (E). In (A), steps were 3.5 s in duration with 1.5 s tail steps. In (B), steps were 500 ms in duration with 250 ms tail steps. For (C)–(E), steps were 1500 ms in duration, with tail steps of 500 ms. (A) Currents were recorded from an oocyte injected with mRNA encoding the Kv10.1 gene. No significant current is present, suggesting that Kv10.1 does not form functional voltage-gated channels as a homomultimer. (B) Currents recorded from an oocyte injected with mRNA from both Kv10.1 and Kv2.1. The characteristic Kv2.1 current shown in panel (C) is absent. This indicates that Kv10.1 monomers are able to coassemble with Kv2.1 monomers. Excess Kv10.1 was injected to eliminate homomultimeric Kv2.1 channels. (C) Currents recorded from an oocyte injected with 1/10 the amount of Kv2.1 mRNA used in (B). Large, voltage-dependent outward potassium currents are seen upon depolarization, despite the lower mRNA concentration. (D) Currents recorded from an oocyte injected with both Kv10.1 and Kv2.2 mRNA. Excess Kv10.1 mRNA was used to eliminate Kv2.2 homomultimers. (E) Homomultimeric Kv2.2 currents recorded from an oocyte injected only with Kv2.2 mRNA. Note the dramatic difference in deactivation rate (arrows) between (D) and (E). This difference and differences in other functional properties (see FIG. 4) indicate that the current observed in (D) is not a homomultimeric Kv2.2 current, but instead is produced by Kv10.1–Kv2.2 heteromultimeric channels.

The present invention provides for the first time nucleic acids encoding members of the Kv10 subfamily of voltage-gated potassium channels. The present invention also provides the sequence of Kv10.1, the first identified member of the Kv10 subfamily. This polypeptide monomer is a member of the Kv family of potassium channels. Members of this family are polypeptide subunits of potassium channels having six transmembrane regions. Expression of the Kv10.1 gene in the Xenopus oocyte system does not produce functional voltage-gated potassium channels (see FIG. 3). However, coexpression of Kv10.1 with either Kv2.1 or Kv2.2 shows that Kv10.1 can modify the properties of other Kv channels through heteromultimer formation. Kv10.1 causes a strong reduction in Kv2.1 current amplitude, probably through the formation of heteromultimers that are either non-functional or can't be gated by voltage alone. In contrast, Kv10.1 increases the activation and deactivation rates of the Kv2.2 current, and causes a depolarized shift in the voltage-dependence of Kv2.2 activation. These properties suggest a role for the modulation of Kv10.1 in the control of neuronal excitability, because Kv2.1 and Kv2.2 comprise the major delayed rectifier potassium current in most neurons.

The invention therefore provides methods of screening for activators and inhibitors of potassium channels that contain a Kv10 subunit. Such modulators of potassium channel activity are useful for treating disorders, including CNS disorders, such as epilepsy and other seizure disorders, Parkinson's disease, migraines, vision problems, psychotic disorders such as schizophrenia and depression, and cognitive disorders such as learning and memory disorders. Such modulators are also useful as neuroprotective agents (e.g., to prevent stroke) and for treatment of pain e.g., neuropathic pain. Such modulators are also useful for treating vision disorder involving abnormal electrical signaling in the retina. Finally, such modulators are also useful for treating prostate hyperplasia, for controlling spermatocyte maturation and motility, for treating infertility, and as contraceptive agents.

Furthermore, the invention provides assays for Kv10 activity where Kv10.1 acts as a direct or indirect reporter molecule. Such uses of Kv10 as a reporter molecule in assay and detection systems have broad applications, e.g., Kv10 can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, Kv10 can be used as an indicator of current flow in a particular direction (e.g., outward or inward potassium flow), and in another embodiment, Kv10 can be used as an indirect reporter via attachment to a second reporter molecule such as green fluorescent protein.

The invention also provides for methods of detecting Kv10 nucleic acid and protein expression, allowing investigation of the channel diversity provided by Kv10 family members, as well as diagnosis of disorders, including CNS disorders, such as epilepsy and other seizure disorders, Parkinson's disease, migraines, psychotic disorders such as schizophrenia and depression, cognitive disorders such as learning and memory disorders, neuropathic pain, vision disorders, prostate hyperplasia, spermatocyte maturation and motility disorders, and infertility.

Finally, the invention provides for a method of screening for mutations of hKv10 genes or proteins. The invention includes, but is not limited to, methods of screening for mutations in hKv10 with the use of a computer. Similarly, the invention provides for methods of identifying the three-dimensional structure of Kv10 polypeptides, e.g., Kv10.1, as well as the resulting computer readable images or data that comprise the three dimensional structure of Kv10 polypeptides. Other methods for screening for mutations of hKv10 genes or proteins include high density oligonucleotide arrays, PCR, immunoassays and the like.

Functionally, Kv10 polypeptides are alpha subunits of a Kv potassium channel. Kv10.1 channels are voltage gated. Typically, such channels are heteromeric or homomeric and contain four alpha subunits or monomers each with six transmembrane domains. Heteromeric Kv channels can comprise one or more Kv10 alpha subunits along with one or more additional alpha subunits from the Kv family, such as Kv2 channels, e.g., Kv2.1 and 2.2. Kv10 channels may also be homomeric. In addition, such channels may comprise one or more auxiliary beta subunits. The presence of Kv10 in a potassium channel may also modulate the activity of the heteromeric channel and thus enhance channel diversity. Channel diversity is also enhanced with alternatively spliced forms of Kv10 genes. Kv10.1 nucleic acids have been isolated from cDNAs from the human brain and retina.

Structurally, the nucleotide sequence of human Kv10.1 (SEQ ID NOS:1–2) encodes a polypeptide monomer with a predicted molecular weight of approximately 62.5 kD and a predicted molecular weight range of 58–68 kD. In particular, the amino acid sequence of Kv10.1 has a conserved region corresponding to amino acids 102–514. Related Kv10.1 genes from other species and members of the Kv10 subfamily share at least about 60%, preferably 65%, 70%, 75%, 80%, 85%, 90% or 95% amino acid identity in the conserved region.

The present invention also provides polymorphic variants of the human Kv10.1 depicted in SEQ ID NO:3: variant #1, in which an valine residue is substituted for the leucine residue at amino acid position 99; variant #2, in which a leucine residue is substituted for the methionine acid residue at amino acid position 285; variant #3, in which a methionine residue is substituted for the valine residue at amino acid position 518; and variant #4, in which an glutamic acid residue is substituted for the glutamine residue at amino acid position 77.

Specific regions of Kv10 nucleotide and amino acid sequence may be used to identify Kv10 subfamily members, and Kv10.1 polymorphic variants, interspecies homologs, and alleles. This identification can be made in vitro, e.g., under stringent hybridization conditions and sequencing, or by using the sequence information in a computer system for comparison with other nucleotide sequences, or using antibodies raised to Kv10.1Typically, identification of Kv10 subfamily members and Kv10.1 polymorphic variants, orthologs, and alleles is made by comparing the amino acid sequence (or the nucleic acid encoding the amino acid sequence) of a conserved region corresponding to amino acids 102–514 of SEQ ID NO:3. Amino acid identity of approximately at least 60% or above, preferably 70%, 65%, 75%, 80%, 85%, most preferably 90–95% or above in the conserved region (amino acids 102–514 of SEQ ID NO:3) typically demonstrates that a protein is a Kv10 subfamily member or a Kv10.1 polymorphic variant, interspecies homolog, or allele. Sequence comparison is typically performed using the BLAST or BLAST 2.0 algorithm with default parameters, discussed below.

Kv10 subfamily members and Kv10.1 polymorphic variants, interspecies homologs, and alleles can be confirmed by expressing or co-expressing the putative Kv10 polypeptide monomer and examining whether it forms a potassium channel with Kv family functional characteristics, and Kv10 characteristics such as rapid activation and deactivation. This assay is used to demonstrate that a protein having about 60% or greater, preferably 65%, 70%, 75%, 80%, 85%, 90%, or 95% or greater amino acid identity to the conserved region of Kv10.1 shares the same functional characteristics as Kv10.1 and is therefore a species of Kv10.1 or a member of the Kv10 subfamily. Typically, human Kv10.1 having the amino acid sequence of SEQ ID NO: 3 is used as a positive control in comparison to the putative Kv10 protein to demonstrate the identification of a Kv10 subfamily member or a Kv10.1 polymorphic variant, ortholog, conservatively-modified variant, mutant, or allele.

Kv10.1 nucleotide and amino acid sequence information may also be used to construct models of voltage-gated potassium channels in a computer system. These models are subsequently used to identify compounds that can activate or inhibit voltage-gated potassium channels comprising Kv10 polypeptides. Such compounds that modulate the activity of channels comprising Kv10 polypeptides, e.g., Kv10.1, can be used to investigate the role of Kv10 polypeptides in modulation of channel activity and in channel diversity.

The isolation of biologically active Kv10.1 for the first time provides a means for assaying for inhibitors and activators of voltage-gated potassium channels that comprise Kv10 subunits. Biologically active Kv10 polypeptides is useful for testing inhibitors and activators of voltage-gated potassium channels comprising subunits of Kv10 and/or other Kv members such as Kv2, e.g., Kv2.2 and 2.2, using in vivo and in vitro expression that measure, e.g., changes in voltage or current. Such activators and inhibitors identified using a potassium channel comprising at least one Kv10 subunit, e.g., Kv10.1, optionally up to four Kv10 subunits, can be used to further study voltage gating, channel kinetics and conductance properties of potassium channels. Such activators and inhibitors are useful as pharmaceutical agents for treating diseases involving abnormal ion flux, e.g., disorders, including CNS disorders, such as epilepsy and other seizure disorders, Parkinson's disease, migraines, psychotic disorders such as schizophrenia and depression, cognitive disorders such as learning and memory disorders, neuropathic pain, vision disorders, prostate hyperplasia, spermatocyte maturation and motility disorders, and infertility, as described above. Modulators are also useful as neuroprotective agents (e.g., to prevent stroke)., as described above. Methods of detecting Kv10 nucleic acids and polypeptides and expression of channels comprising Kv10 polypeptides are also useful for diagnostic applications for diseases involving abnormal ion flux, e.g., as described above. For example, chromosome localization of the gene encoding human Kv10.1 can be used to identify diseases caused by and associated with Kv10.1. Methods of detecting Kv10.1 are also useful for examining the role of Kv10.1 in channel diversity and modulation of channel activity.

II. DEFINITIONS

As used herein, the following terms have the meanings ascribed to them unless specified otherwise.

The phrase "conserved region" refers to the region of Kv10.1 that structurally identifies this particular protein (approximately amino acids 102–514 of SEQ ID NO:3). This region can be used to identify Kv10 subfamily members as well as Kv10.1 polymorphic variants, orthologs, conservatively modified variants, mutants, and alleles, each of which will typically comprise at least about 60%, 65%, 70%, 75%, 80%, 85%, 90%, 95%, or greater amino acid sequence identity to the conserved region, through amino acid sequence identity comparison using a sequence comparison algorithm such as BLASTP, using the parameters described herein.

"Kv10" and "Kv10.1" refer to a polypeptide that is a subunit or monomer of a Kv potassium channel, and a member of the Kv family. When Kv10 is part of a potassium channel, either a homomeric or heteromeric potassium channel, the channel has the characteristic of voltage gating and rapid activation and deactivation. The terms Kv10 and Kv10.1 therefore refer to Kv10 subfamily members and Kv10.1 polymorphic variants, alleles, mutants, and interspecies homologs that: (1) have a subsequence that has greater than about 60% amino acid sequence identity, preferably about 65%, 70%, 75%, 80%85%, 90%, or 95% amino acid sequence identity, to the Kv10 conserved region (amino acids 102–514 of SEQ ID NO:3), or, optimally, comprise 60%, 65%, 70%, 75%, 80%, 85%, 90%, 95%, or greater identity to a Kv10.1 amino acid sequence of SEQ ID NO:3; (2) bind to antibodies, e.g., polyclonal antibodies, raised against an immunogen comprising an amino acid sequence of SEQ ID NO:3 or amino acids 102–514 of SEQ ID NO:3, and conservatively modified variants thereof; (3) specifically hybridize under stringent hybridization conditions to a sequence of SEQ ID NOS:1–2 or a nucleotide sequence encoding amino acids 102–514 of SEQ ID NO:3, and conservatively modified variants thereof; or (4) are amplified by primers that specifically hybridize under stringent hybridization conditions to the same sequence as a primer set selected from the group consisting of SEQ ID NOS:4–11.

The phrase "voltage-gated" activity or "voltage-gating" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the membrane potential for potassium ($E_K$) in typical cells. $E_K$, or the membrane potential for potassium, depends on the relative concentrations of potassium found inside and outside the cell membrane, and is typically between −60 and −100 mV for mammalian cells. $E_K$ is the membrane potential at which there is no net flow of potassium ion because the electrical potential (i.e., voltage potential) driving potassium influx is balanced by the concentration gradient (the [$K^+$] potential) directing potassium efflux. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Nonner, in *Potassium Channels*, pp. 40–60 (Cook, ed., 1990)). The characteristic of voltage gating can be measured by a variety of techniques for measuring changes in current flow and ion flux through a channel, e.g., by changing the [$K^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

"Homomeric channel" refers to a Kv10 channel composed of identical alpha subunits, whereas "heteromeric channel" refers to a Kv10 channel composed of at least one Kv10 alpha subunit, e.g., Kv10.1, plus at least one other different type of alpha subunit from another Kv subfamily such as Kv2, e.g., Kv2.1 or 2.2. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "functional effects" in the context of assays for testing compounds affecting a channel comprising Kv10 includes the determination of any parameter that is indirectly or directly under the influence of the channel. It includes physical and chemical effects, e.g., changes in ion flux and membrane potential, changes in ligand binding, and also includes other physiologic effects such as increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., potassium, rubidium. Preferably, the term refers to the functional effect of the compound on the channels comprising Kv10, e.g., changes in ion flux including radioisotopes, current amplitude, membrane potential, current flow, transcription, protein binding, phosphorylation, dephosphorylation, second messenger concentrations (cAMP, cGMP, $Ca^{2+}$, $IP_3$), ligand binding, changes in ion concentration, and other physiological effects such as hormone and neurotransmitter release, as well as changes in voltage and current. Such functional effects can be measured by any means known to those skilled in the art, e.g., patch clamping, voltage-sensitive dyes, ion sensitive dyes, whole cell currents, radio-isotope efflux, inducible markers, and the like.

"Inhibitors," "activators" or "modulators" of voltage-gated potassium channels comprising a Kv10 polypeptide refer to inhibitory or activating molecules identified using in vitro and in vivo assays for Kv10 channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing a Kv10 polypeptide, e.g., Kv10.1, in cells or cell membranes and then measuring flux of ions through the channel and determining changes in polarization (i.e., electrical potential). Alternatively, cells expressing endogenous Kv10 channels can be used in such assays. To examine the extent of inhibition, samples or assays comprising a Kv10 channel are treated with a potential activator or inhibitor and are compared to control samples without the inhibitor. Control samples (untreated with inhibitors) are assigned a relative Kv10 activity value of 100%. Inhibition of channels comprising Kv10 is achieved when the Kv10 activity value relative to the control is about 90%, preferably 50%, more preferably 25–0%. Activation of channels comprising Kv10 is achieved when the Kv10 activity value relative to the control is 110%, more preferably 150%, most preferably at least 200–500% higher or 1000% or higher.

"Biologically active" Kv10 polypeptides refers to Kv10 polypeptides, e.g., Kv10.1, that have the ability to form a potassium channel having the characteristic of voltage-gating tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated Kv10 nucleic acid is separated from open reading frames that flank the Kv10 gene and encode proteins other than Kv10. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}$p, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:3 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as amino acids 102–514 of SEQ ID NO:3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to Kv10 nucleic acids and proteins, e.g., Kv10.1, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

An "anti-Kv10" antibody is an antibody or antibody fragment that specifically binds a polypeptide encoded by a Kv10 gene, cDNA, or a subsequence thereof, e.g., Kv10.1.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to Kv10.1, as shown in SEQ ID NO:3, or splice variants, or portions thereof, can be selected to obtain only those polyclonal antibodies that are specifically immunoreactive with Kv10 subfamily members and not with other proteins. This selection may be achieved by subtracting out antibodies that cross-react with molecules such as other Kv family members. In addition, polyclonal antibodies raised to Kv10.1 polymorphic variants, alleles, orthologs, and conservatively modified variants can be selected to obtain only those antibodies that recognize Kv10.1, but not other Kv10 subfamily members. In addition, antibodies to human Kv10.1 but not other Kv10.1 orthologs can be selected in the same manner. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains Kv10 polypeptides or nucleic acid encoding a Kv10 protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. ISOLATING A GENE ENCODING A Kv10 POLYPEPTIDE

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding Kv10 Polypeptides In general, the nucleic acid sequences encoding Kv10.1 and related nucleic acid sequence homologs such as other Kv10 subfamily members are cloned from cDNA and genomic DNA libraries or isolated using amplification techniques with oligonucleotide primers. For example, Kv10.1 sequences are typically isolated from human nucleic acid (genomic or cDNA) libraries by hybridizing with a nucleic acid probe or polynucleotide, the sequence of which can be derived from SEQ ID NOS:1–2, preferably from the region encoding the conserved region (see, e.g., amino acids 102 to 514 of SEQ ID NO:3). A suitable tissue from which Kv10.1 RNA and cDNA can be isolated is nervous system tissue such as whole brain, or retina.

Amplification techniques using primers can also be used to amplify and isolate Kv10.1 and other Kv10 subfamily members from DNA or RNA. The following primers can also be used to amplify a sequence of human Kv10.1:

GCCATGCTCAAACAGAGTGAGAGGAGAC (SEQ ID NO:4)

GAGCGTGAAGAAGCCCATGCACAG (SEQ ID NO:5)

GCAGCACCCCGGACAGGTAGAAA (SEQ ID NO:6)

CGGCCGGGTCGCGGTCGAAGAAGT (SEQ ID NO:7)

CCACCATGAGGGCAGCCAACACCGCAGGAGCA (SEQ NO:8)

GGCTGTCTACTCTGTGGAGCACGAT (SEQ ID NO:9)

GAGTATTTCTAGAGGCAGTACTTTGTG (SEQ ID NO:10) and

ATTCTCTTGTCTTGGGGTGAGCTG (SEQ ID NO:11)

These primers can be used, e.g., to amplify either the full length sequence or a probe of one to several hundred nucleotides, which is then used to screen a library for full-length Kv10.1.

Nucleic acids encoding Kv10.1 and other Kv10 family members can also be isolated from expression libraries using antibodies as probes. Such polyclonal or monoclonal antibodies can be raised using the sequence of SEQ ID NO:3, or an immunogenic portion thereof, e.g., amino acids 102 to 514 of SEQ ID NO:3.

Kv10 subfamily members and Kv10.1 polymorphic variants, orthologs, and alleles that are substantially identical to the conserved region of Kv10.1 can be isolated using Kv10.1 nucleic acid probes and oligonucleotides under stringent hybridization conditions, by screening libraries. Alternatively, expression libraries can be used to clone Kv10 subfamily members and Kv10.1 and Kv10.1 polymorphic variants, orthologs, and alleles by detecting expressed homologs immunologically with antisera or purified antibodies made against human Kv10.1 or portions thereof (e.g., the conserved region of human Kv10.1), which also recognize and selectively bind to the Kv10.1 homolog.

To make a cDNA library, one should choose a source that is rich in Kv10 mRNA, e.g., human Kv10.1 mRNA, e.g., nervous system tissue such as whole brain or retina. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating Kv10 subfamily members and Kv10.1 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human Kv10.1 directly from mRNA, from cDNA, from genomic libraries or cDNA libraries. Degenerate oligonucleotides can be designed to amplify Kv10.1 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Kv10.1 encoding mRNA in physiological samples, for nucleic acid sequencing, or for other purposes. Genes amplified by the PCR reaction can be purified from agarose gels and cloned into an appropriate vector.

Gene expression of Kv10 subfamily members and Kv10.1 can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology and the like.

Synthetic oligonucleotides can be used to construct recombinant Kv10 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the Kv10.1 gene. The specific subsequence is then ligated into an expression vector.

The gene for Kv10 subfamily members, e.g., Kv10.1 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding a Kv10 subfamily member such ad Kv10.1, one typically subclones Kv10.1 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the Kv10.1 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Kv10 encoding nucleic acid in host cells. A typical expression cassette thus contains a promoter operably linked to the nucleic acid sequence encoding Kv10 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a Kv10 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of Kv10 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Kv10.

After the expression vector is introduced into the cells, the transfected cells are cultured under conditions favoring expression of Kv10, which is recovered from the culture using standard techniques identified below.

IV. PURIFICATION OF Kv10 POLYPEPTIDES

Either naturally occurring or recombinant Kv10 subfamily members such as Kv10.1 can be purified for use in functional assays. Naturally occurring Kv10.1 monomers can be purified, e.g., from human tissue such as whole brain or retina and any other source of a Kv10.1 homolog. Recombinant Kv10 monomers can be purified from any suitable expression system.

The Kv10 monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra, and Sambrook et al., supra).

A number of procedures can be employed when recombinant Kv10 monomers are being purified. For example, proteins having established molecular adhesion properties can be reversible fused to the Kv10 monomers. With the appropriate ligand, the Kv10 monomers can be selectively adsorbed to a purification column and then freed from the column in a relatively pure form. The fused protein is then removed by enzymatic activity. Finally the Kv10 monomers could be purified using immunoaffinity columns.

A. Purification of Kv10 Monomers From Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the Kv10 monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human Kv monomers are separated from other bacterial proteins by standard separation techniques, e.g., with Ni-NTA agarose resin.

Alternatively, it is possible to purify the Kv10 monomers from bacteria periplasm. After lysis of the bacteria, when the Kv10 monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Kv10 Monomers Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the Kv10 monomers can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The Kv10 monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. IMMUNOLOGICAL DETECTION OF Kv10 POLYPEPTIDES

In addition to the detection of Kv10 genes and gene expression using nucleic acid hybridization technology, one can also use immunoassays to detect the Kv10 monomers of the invention. Immunoassays can be used to qualitatively or quantitatively analyze the hKv10 monomers. A general overview of the applicable technology can be found in Harlow & Lane, Antibodies: *A Laboratory Manual* (1988).

A. Antibodies to Kv10 and 10.1 Monomers

Methods of producing polyclonal and monoclonal antibodies that react specifically with the Kv10 monomers, Kv10.1 monomers, or Kv10.1 monomers from particular species such as human Kv10.1 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, Nature 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of Kv10.1 monomers may be used to produce antibodies specifically reactive with Kv10 monomers. For example, recombinant Kv10.1 monomers or an antigenic fragment thereof, such as the conserved region (see, e.g., amino acids 102–514 of SEQ ID NO:3), can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Kv family proteins and other Kv family proteins, using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better. Antibodies specific only for a particular Kv10.1 ortholog, such as human Kv10.1, can also be made, by subtracting out other cross-reacting orthologs from a species such as a non-human mammal.

Once the specific antibodies against a Kv10.1 are available, the Kv10 subfamily members such as Kv10.1 can be detected by a variety of immunoassay methods. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The Kv10 polypeptides of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991). Immunological binding assays (or immunoassays) typically use an antibody that specifically binds to a protein or antigen of choice (in this case the Kv10 subfamily member or Kv10.1 or an antigenic subsequence thereof). The antibody (e.g., anti-Kv10) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Kv10 polypeptide or a labeled anti-Kv10 antibody. Alternatively, the labeling agent may be a third moiety, such a secondary antibody, which specifically binds to the antibody/Kv10 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting the Kv10 in samples may be either competitive or noncompetitive. Noncompetitive immunoassays are assays in which the amount of antigen is directly measured. In one preferred "sandwich" assay, for example, the anti-Kv10 subunit antibodies can be bound directly to a solid substrate on which they are immobilized. These immobilized antibodies then capture Kv10 present in the test sample. The Kv10 monomers are thus immobilized and then bound by a labeling agent, such as a second Kv10 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the Kv10 present in the sample is measured indirectly by measuring the amount of known, added (exogenous) Kv10 displaced (competed away) from an anti-Kv10 antibody by the unknown Kv10 present in a sample. In one competitive assay, a known amount of the Kv10 is added to a sample and the sample is then contacted with an antibody that specifically binds to the Kv10. The amount of exogenous Kv10 bound to the antibody is inversely proportional to the concentration of the Kv10 present in the sample. In a particularly preferred embodiment, the antibody is immobilized on a solid substrate. The amount of Kv10 bound to the antibody may be determined either by measuring the amount of Kv10 present in a Kv10 antibody complex, or alternatively by measuring the amount of remaining uncomplexed protein. The amount of Kv10 may be detected by providing a labeled Kv10 molecule.

A hapten inhibition assay is another preferred competitive assay. In this assay the known Kv10 is immobilized on a solid substrate. A known amount of anti-Kv10 antibody is added to the sample, and the sample is then contacted with the immobilized Kv10. The amount of anti-Kv10 antibody bound to the known immobilized Kv10 is inversely proportional to the amount of Kv10 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations for Kv10 subfamily members and Kv10.1. For example, a Kv10.1 protein at least partially corresponding to an amino acid sequence of SEQ ID NO:3 or an immunogenic region thereof, such as the conserved region (e.g., amino acids 102–514 of SEQ ID NO:3), can be immobilized to a solid support. Other proteins such as other Kv family members are added to the assay so as to compete for binding of the antisera to the immobilized antigen. The ability of the added proteins to compete for binding of the antisera to the immobilized protein is compared to the ability of the Kv10.1 or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. Antibodies that specifically bind only to Kv10 subfamily members, or only to particular orthologs of Kv10.1, such as human Kv10.1, can also be made using this methodology.

The immunoabsorbed and pooled antisera are then used in a competitive binding immunoassay as described above to compare a second protein, thought to be perhaps a Kv10 subfamily member or an allele, ortholog, or polymorphic variant of Kv10.1, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by Kv10.1 that is required to inhibit 50% of binding, then the second protein is said to specifically bind to the polyclonal antibodies generated to the respective Kv10.1 immunogen.

Other Assay Formats

Western blot (immunoblot) analysis is used to detect and quantify the presence of the Kv10 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind Kv10. The anti-Kv10 antibodies specifically bind to Kv10 on the solid support. These antibodies may be directly labeled or alternatively may be subsequently detected using labeled antibodies (e.g., labeled sheep anti-mouse antibodies) that specifically bind to the anti-Kv10 antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$p), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize hKv10, or secondary antibodies that recognize anti-hKv10 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. ASSAYS FOR MODULATORS OF Kv10

A. Assays

Human Kv10 subfamily monomers and Kv10.1 alleles, orthologs, and polymorphic variants are subunits of potassium channels. The activity of a potassium channel comprising Kv10 can be assessed using a variety of in vitro and in vivo assays, e.g., measuring current, measuring membrane potential, measuring ligand binding, measuring ion flux, e.g., potassium, or rubidium, measuring ion concentration, measuring second messengers and transcription levels, using potassium-dependent yeast growth assays, measuring ligand binding, and using, e.g., voltage-sensitive dyes, ion sensitive dyes such as potassium sensitive dyes, radioactive tracers, and patch-clamp electrophysiology.

Furthermore, such assays can be used to test for inhibitors and activators of channels comprising Kv10, e.g., Kv10.1. Such modulators of a potassium channel are useful for treating various disorders involving potassium channels. Treatment of dysfunctions include, e.g., CNS disorders, such as epilepsy, migraines, vision problems, psychotic disorders such as schizophrenia and depression, seizures, and cognitive disorders such as learning and memory disorders. Such modulators are also useful as neuroprotective agents (e.g., to prevent stroke) and for treatment of pain, e.g., neuropathic pain. Such modulators are also useful for investigation of the channel diversity provided by Kv10 subfamily members and the regulation/modulation of potassium channel activity provided by Kv10 subfamily members such as Kv10.1.

Modulators of the Kv potassium channels are tested using biologically active Kv10, either recombinant or naturally occurring, preferably human Kv10.1. Kv10 can be isolated, co-expressed or expressed in a cell, or expressed in a membrane derived from a cell. In such assays, Kv10 is expressed alone to form a homomeric potassium channel or is co-expressed with a second alpha subunit (e.g., another Kv family member, e.g., Kv2, preferably Kv2.1 or Kv2.2) so as to form a heteromeric potassium channel. Kv10 polypeptides can also be expressed with additional beta subunits. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising a Kv10 polypeptide is achieved when the potassium channel activity value relative to the control is about 90%, preferably 50%, more preferably 25%. Activation of channels comprising a Kv10 polypeptide is achieved when the potassium channel activity value relative to the control is 110%, more preferably 150%, more preferable 200% higher. Compounds that increase the flux of ions will cause a detectable increase in the ion current density by increasing the probability of a channel comprising a Kv10 polypeptide being open, by decreasing the probability of it being closed, by increasing conductance through the channel, and/or by allowing the passage of ions.

Changes in ion flux may be assessed by determining changes in polarization (i.e., electrical potential) of the cell or membrane expressing the potassium channel comprising a Kv10 polypeptide. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes or ion sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising a Kv10 polypeptide can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The ions can be measured in a variety of standard ways. They can be measured directly by concentration changes of the ions, e.g., changes in intracellular concentrations, or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

Preferably, the Kv10 polypeptide that is a part of the potassium channel used in the assay will have the sequence displayed in SEQ ID NO:3 or a conservatively modified variant thereof. Alternatively, the Kv10 of the assay will be derived from a eukaryote and include an amino acid subsequence having substantial amino acid sequence identity to the conserved region (see, e.g., amino acids 102 to 514 of SEQ ID NO:3) of human Kv10.1. Generally, the amino acid sequence identity will be at least 60%, preferably at least 65%, 70%, 75%, 80%, 85%, or 90%, most preferably at least 95%.

Kv10 subfamily members and Kv10.1 orthologs, alleles, polymorphic variants, and conservatively modified variants will generally confer substantially similar properties on a channel comprising a Kv10 polypeptide, as described above. In a preferred embodiment, the cell placed in contact with a compound that is suspected to be a Kv10 homolog is assayed for increasing or decreasing ion flux in a eukaryotic cell, e.g., an oocyte of Xenopus (e.g., *Xenopus laevis*) or a mammalian cell such as a CHO or HeLa cell. Channels that are affected by compounds in ways similar to Kv10.1 are considered homologs or orthologs of Kv10 subfamily members such as Kv10.1.

B. Modulators

The compounds tested as modulators of Kv channels comprising a Kv10 subunit can be any small chemical compound, or a biological entity, such as a protein, sugar, nucleic acid or lipid. Alternatively, modulators can be genetically altered versions of a Kv10 subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a Kv channel comprising a human Kv10.1 subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds are possible using the integrated systems of the invention.

C. Solid State and Soluble High Throughput Assays

In one embodiment the invention provides soluble assays using potassium channels comprising a Kv10 polypeptide, e.g., Kv10.1; a membrane comprising a Kv10 potassium channel, or a cell or tissue expressing potassium channels comprising a Kv10 polypeptide, either naturally occurring or recombinant. In another embodiment, the invention provides solid phase based in vitro assays in a high throughput format, where Kv10 potassium channel attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

The channel of interest, or a cell or membrane comprising the channel of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. COMPUTER ASSISTED DRUG DESIGN USING hKv10

Yet another assay for compounds that modulate the activities of a Kv10 channel involves computer assisted drug design, in which a computer system is used to generate a three-dimensional structure of Kv10.1 based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where Kv10.1 interacts with other potassium channel subunits.

The three-dimensional structural model of the protein is generated by entering channel protein amino acid sequences of at least 25, 50, 75 or 100 amino acid residues or corresponding nucleic acid sequences encoding a Kv10.1 monomer into the computer system. The amino acid sequence of each of the monomers is selected from the group consisting of SEQ ID NO:3 and a conservatively modified versions thereof, or an immunogenic portion thereof comprising amino acids 102–514 of SEQ ID NO:3. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the Kv10 protein to identify ligands that bind to Kv10subfamily members such as Kv10.1. Binding affinity between the protein and ligands is determined using energy terms to determine which ligands have an enhanced probability of binding to the protein.

Computer systems are also used to screen for mutations, polymorphic variants, alleles and interspecies homologs of Kv10 subfamily member genes such as Kv10.1. Such mutations can be associated with disease states. Once the variants are identified, diagnostic assays can be used to identify patients having such mutated genes associated with disease states. Identification of the mutated Kv10 genes involves receiving input of a first nucleic acid, e.g., SEQ ID NOS:1–2, or an amino acid sequence encoding Kv10.1, e.g., SEQ ID NO:3, and conservatively modified versions thereof, or an amino acid sequence comprising amino acids 102–514 of SEQ ID NO:3. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in Kv10 genes, preferably Kv10.1 genes, more preferably human Kv10.1 genes and mutations associated with disease states. The first and second sequences described above can be saved on a computer readable substrate.

Nucleic acids encoding Kv10 monomers can be used with high density oligonucleotide array technology (e.g., GeneChip™) to identify Kv10 subfamily members and Kv10.1 homologs, orthologs, alleles, conservatively modified variants, and polymorphic variants in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. CELLULAR TRANSFECTION AND GENE THERAPY

The present invention provides the nucleic acids of Kv10 subfamily members for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for Kv10, e.g., Kv10.1, under the control of a promoter, then expresses a Kv10.1 monomer of the present invention, thereby mitigating the effects of absent, partial inactivation, or abnormal expression of the Kv10.1 gene. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Mulligan, *Science* 926–932 (1993); Dillon, *TIBTECH* 11:167–175 (1993); Miller, *Nature* 357:455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin*, 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors (Ellem et al., *Immunol Immunother.* 44(1):10–20 (1997); Dranoff et al., *Hum. Gene Ther.* 1:111–2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 241:5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. PHARMACEUTICAL COMPOSITIONS AND ADMINISTRATION

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the Kv channels comprising a Kv10 subunit, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. KITS

Human Kv10 subfamily members such as Kv10.1 and its homologs are useful tools for examining expression and regulation of potassium channels. Human Kv10 -specific reagents that specifically hybridize to hKv10 nucleic acid, such as hKv10 probes and primers, and hKv10 -specific reagents that specifically bind to the hKv10 protein, e.g., hKv10 antibodies are used to examine expression and regulation.

Nucleic acid assays for the presence of hKv10 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, hKv10 protein can be detected with the various immunoassay techniques described above. The test sample is typically compared to both a positive control (e.g., a sample expressing recombinant Kv10 monomers) and a negative control.

The present invention also provides for kits for screening modulators of the potassium channels of the invention. Such kits can be prepared from readily available materials and reagents. For example, such kits can comprise any one or more of the following materials: Kv10 monomers, reaction tubes, and instructions for testing the activities of potassium channels containing Kv10. A wide variety of kits and components can be prepared according to the present invention, depending upon the intended user of the kit and the particular needs of the user. For example, the kit can be tailored for in vitro or in vivo assays for measuring the activity of a potassium channel comprising a Kv10 monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Cloning of Kv10.1

An approximately 950 bp fragment of Kv10.1 was amplified from human brain cDNA using oligos based on a partial human genomic sequence similar to Kv family potassium channels (Genbank Accession Number AC019222.1). The sense oligo used was 5'-CCGCCATGCTCAAACAGAGTGAGAGGAGAC (Oligo 1; SEQ ID NO:4) and the antisense oligo used was 5'-GAGCGTGAAGAAGCCCATGCACAG (Oligo 2; SEQ ID NO:5). Only the bold type nucleotides in (1) match the Kv10.1 genomic sequence; the two additional nucleotides were added to complete a Kozak sequence upstream of the methionine codon (ATG). This was done to speed expression vector construction if this ATG codon turned out to be the initiator codon. The two nucleotides are not necessary to amplify Kv10.1.

The 5' end of the Kv10.1 reading frame was confirmed using 2 nested rounds of 5' RACE PCR. Human brain cDNA was amplified by standard RACE PCR techniques using the gene-specific antisense oligo 5'-GCAGCACCCCGGACAGGTAGAAA (Oligo 3; SEQ ID NO:6). An aliquot of this reaction was then amplified using the nested gene specific antisense oligo 5'-CGGCCGGGTCGCGGTCGAAGAAGT (Oligo 4; SEQ ID NO:7) to obtain an approximately 600 bp fragment. This fragment overlaps with the 950 bp fragment identified above, and it was determined that the start codon of Kv10.1 was the 5'-most ATG of the 950 bp fragment. Stop codons occur in all reading frames upstream of this methionine codon.

The 3' end of Kv10.1 was obtained in two stages. First, two nested rounds of standard 3' RACE PCR were used to obtain an approximately 1.5 kb fragment. The gene-specific sense oligos used to obtain this fragment were oligo (1) from above in the first round, and the nested oligo 5'-CCACCATGAGGGCAGCCAACACCGCAGGAGCA (Oligo 5; SEQ ID NO:8) in the second round. This fragment overlapped with the 950 bp fragment cloned above, and extended the coding sequence of Kv10.1 by almost 500 bp. Together, they give a contiguous open reading frame for Kv10.1 extending from the initiator methionine to the 5' end of the conserved pore domain of Kv potassium channels. However, the 3' end of this conserved sequence was not found, and a possible intron/exon boundary was present at the point of sequence divergence from other known Kv family channels. Therefore, tried a new 3' RACE reaction was performed using a new gene-specific sense oligo located closer to this region (5'-GGCTGTCTACTCTGTGGAGCACGAT (Oligo 6; SEQ ID NO:9)). Using this technique, an approximately 750 bp fragment was amplified out of human retina cDNA. Sequence analysis of this fragment, which overlaps the original 950 bp fragment of Kv10.1, revealed an entire Kv pore sequence, a region homologous to the S6 domain of Kv channels, and a termination codon. This fragment was overlapped with the original 950 bp fragment and the 5' RACE fragment to obtain a complete coding sequence for Kv10.1.

The entire coding region of Kv10.1 was amplified from human retina cDNA using oligo (1) and the antisense oligo 5'-GAGTATTTCTAGAGGCAGTACTTTGTG (Oligo 7; SEQ ID NO;10), which is based on Kv 10.1 3' untranslated sequence. To amplify the coding region only, (7) can be substituted with 5'- ATTCTCTTGTCTTGGGGTGAGCTG (Oligo 8; SEQ ID NO:11). First strand cDNA from the human retina is the preferred template for amplification of Kv10.1, but first strand cDNA from the human brain is suitable as well. The conditions used to amplify the coding region of Kv10.1 with these oligos were: 24 cycles of 95° C. for 15 seconds, 70–58° C. for 15 seconds (temperature was dropped 0.5° C. each successive cycle), 72° C. for 2 minutes, followed by 20 cycles of 95° C. for 15 seconds, 58° C. for 15 seconds and 72° C. for 2 minutes. An approximately 1.8 kb band was isolated and shown to contain the entire coding region of Kv10.1 by sequence analysis.

The numbered oligonucleotides listed above can be used in various combinations to amplify sections of the Kv10.1 cDNA from an appropriate template using the conditions described above. 1 can be used with 8 to amplify the entire coding sequence (~1.65 kb), with 7 to amplify the coding sequence plus some 3' untranslated sequence (~1.8 kb), with 2 to amplify from the initiator methionine to the S1 domain (~950 bp), and with 4 to amplify ~350 bp from the 5' end of coding sequence. Oligo 5 can be substituted for oligo 1 in any of the above reactions to produce a band that is approximately 60 bp shorter. Oligo 6 can be used with 7 and 8 to produce fragments of approximately 450 bp and 300 bp, respectively. If at least one of these amplifications can be obtained from a gene, and the sequence of the fragment is substantially identical to that of Kv10.1, then the sequence should be considered a species of Kv10.1.

An alignment of the amino acid sequence of Kv10.1 to the amino acid sequences of human Kv2.1 and Kv2.2, the two known genes most homologous to Kv10.1. Kv10.1 is less than 40% identical to Kv2.1 and Kv2.2. In contrast, Kv2.1 and Kv2.2 share over 60% amino acid identity. Therefore Kv10.1 does not represent a novel member of the Kv2 subfamily of Kv potassium channel genes, but is the first representative of a novel family of Kv potassium channels. Since this is the 10th Kv subfamily identified, the gene is named Kv10.1, and the subfamily is named Kv10. The alignment in FIGS. 1A, 1B and 1C also show the best region that can be used to define the Kv10.1 species. Substantial conservation with the Kv2.1 channels begins at amino acid 102, the beginning of the tetramerization domain (T1) of Kv potassium channels. The conservation ends near amino acid 514, in the C-terminal cytoplasmic domain of these Kv channels. Within this region, Kv10.1 shares approximately 40% amino acid identity to Kv2.1 and Kv2.2. Members of the same Kv subfamily typically share higher homology within this region. For instance, Kv2.1 and Kv2.2 are more than 90% identical over the same region. A protein sharing more than of 60% amino acid identity to Kv10.1 in this region is a member of the Kv10 subfamily of potassium channels.

Kv potassium channels are known to be involved in a wide array of physiological processes such as contributing to the electrical properties of neurons, cardiac myocytes and other excitable cells, modulating cell proliferation, control of secretion, and contributing to resting potentials. Kv channels are tetrameric proteins, and most Kv channel proteins can form functional homotetrameric channels (all four subunits are identical). However, a certain subclass of Kv potassium channels (members of the Kv5, Kv6, Kv8 and Kv9 subfamilies) are electrically silent as homotetramers. They only form functional channels when they form heterotetramers with members of the Kv2 subfamily (Kv2.1 and Kv2.2). These channels have several distinct differences from other Kv channels in the S6 transmembrane region. Because Kv10.1 shares many of these differences (FIG. 2), it seemed likely that Kv10 would represent a novel class of electrically silent Kv channels capable of forming heteromultimers with other Kv channels such as Kv2.1 and Kv2.2.

Example 2
Expression of Kv10.1 in Xenopus Oocztes

When expressed in Xenopus oocytes, Kv10.1 is indeed electrically silent. FIG. 3(A) shows that no voltage-dependent potassium currents are detected in oocytes injected with Kv10.1 mRNA, indicating that Kv10.1 can't form functional voltage-gated potassium channels as a homomultimer. It remains possible that Kv10.1 homomultimers are functional, but gated by a stimulus other than voltage. Like other electrically silent Kv subunits, Kv10.1 is able to modify the properties of channels expressed by Kv2 family potassium channel genes. FIGS. 3(B) and 3(C) show that when coexpressed with Kv2.1, Kv10.1 causes a strong reduction in the Kv2.1 current. This suggests that Kv10.1 and Kv2.1 subunits can associate, but that the resultant heteromultimers are either non-functional or not gated by voltage alone. In contrast, FIGS. 3(D), 3(E) and 4 show that Kv10.1forms functional heteromultimers with Kv2.2. The Kv10.1–Kv2.2 heteromultimers are voltage-gated, but activate and deactivate more rapidly than Kv2.2 homomultimers. There is also a pronounced depolarized shift in the voltage-dependence of activation of Kv10.1–Kv2.2 heteromultimers.

Kv2 family channels are present in most neurons, where they serve as the main delayed rectifier potassium current (Murakoshi & Trimmer, *J Neurosci.* 19(5):1728–1735 (1999), Du et al., *Neurosci.*, 84(1):37–48 (1998); Fink et al., *J. Biol. Chem.*, 271:26341–2634 (1996)). Expression of Kv10.1 in the same neuron as a Kv2 family channel will alter the functional role of those channels. Kv10.1 could greatly reduce the delayed rectifier current density in cells expressing both Kv10.1 and Kv2.1. This would limit the contribution of the delayed rectifier to regulation of the electrical properties of such neurons. Coexpression of Kv10.1 and Kv2.2 in neurons would limit the contribution of the delayed rectifier at hyperpolarized voltages because of the depolarized shift in the voltage-dependence of activation and rapid deactivation upon repolarization (FIG. 4(B)). However, the contribution of the delayed rectifier to shaping electrical activity at depolarized voltages would be enhanced because of the rapid activation of Kv10.1–2.2 heteromultimers.

Example 3
RT-PCR Analysis of Kv10.1 Gene Expression cDNA was prepared from either human total RNA samples or human mRNA samples using standard oligo dT priming techniques. $\frac{1}{50}^{th}$ of each cDNA was then amplified for 35 cycles using the Kv10.1-specific primers 5'-TGGGCTGCCTGCTGCTCTTCAT-3' (SEQ ID NO:17) and 5'-CTCTCCCCTCTCCCTGCGTATGGT-3' (SEQ ID NO: 18). Each cycle consisted of a denaturing step to 95° C. for 20 seconds and an annealing/extension step to 63° C. for 40 seconds. Amplification of Kv10.1 under these circumstances leads to the production of a 320 bp fragment. Relative expression levels of Kv10.1 mRNA in the human RNA samples were determined by scoring the presence and intensity of this fragment.

High levels of Kv10.1 expression were found in retina, testis and prostate (FIG. 5). Expression was also found at lower levels in spinal cord and substantia nigra. Trace levels of expression could be detected in frontal cortex and whole brain samples. The low levels of Kv10.1 detected in the whole brain sample could be reflective of the Kv10.1 expression that was found in spinal cord, frontal cortex and substantia nigra. It may also suggest low levels of Kv10.1 expression in other brain regions that were not tested in this assay.

Kv10.1 is expressed in the central nervous system, suggesting that it is coexpressed with Kv2 family channels such as Kv2.1 and 2.2 in at least a subset of neurons. In addition, RT-PCR shows that Kv10.1 is highly expressed in the human retina. Since Kv2 family channels such as Kv2.1 and 2.2 are also expressed in the retina, it is likely that Kv10.1–Kv2 heteromultimers are present in visual system neurons as well. Because of the importance of the delayed rectifier current to the control of neuronal electrical activity, modulators of potassium channels containing Kv10.1 subunits are useful in treating a variety of CNS disorders that involve abnormalities in excitability.

The expression in substantia nigra and frontal cortex suggests a potential role for Kv10.1 modulators in the treatment of Parkinson's disease and psychotic disorders such as schizophrenia and depression. The Kv10.1 expression in spinal cord indicates indicate that Kv10.1 modulators could be used to treat include epilepsy and other seizure disorders, migraines and cognitive disorders. These modulators are also useful for neuroprotection. The high level of Kv10.1 expression in retina indicates that Kv10.1 play a particularly important role in retinal excitability. Modulators of Kv10.1 are thus useful for treating a variety of vision disorders that involve abnormal electrical signaling in the retina.

Kv10.1 expression in prostate suggests a role in treating prostate hyperplasia. Kv10.1 modulators may be able to relax prostate smooth muscle and help relieve the obstructions caused by prostate hyperplasia. Kv10.1 modulators may also be useful in reducing cell proliferation in this condition. The high expression of Kv10.1 in testis suggests that Kv10.1 modulators are useful for controlling spermatocyte maturation and motility. Such modulators are useful in treating certain cases of male infertility and as contraceptive agents.

What is claimed is:

1. An isolated nucleic acid encoding a polypeptide comprising an alpha subunit of a Kv potassium channel, the polypeptide:
   (i) forming, with at least one additional Kv alpha subunit, a Kv potassium channel having the characteristic of voltage-gating; and
   (ii) comprising an amino acid sequence having at least 90% amino acid sequence identity to SEQ ID NO:3.

2. The nucleic acid of claim 1, wherein the nucleic acid encodes an amino acid sequence comprising the sequence of SEQ ID NO:3.

3. The nucleic acid of claim 1, wherein the nucleic acid comprises a nucleotide sequence of SEQ ID NO:1 or SEQ ID NO:2.

4. An expression vector comprising the nucleic acid of claim 1.

5. An isolated host cell transfected with the vector of claim 4.

* * * * *

SEQUENCE LISTING

<160> NUMBER OF SEQ ID NOS: 18

<210> SEQ ID NO 1
<211> LENGTH: 2103
<212> TYPE: DNA
<213> ORGANISM: Homo sapiens
<220> FEATURE:
<223> OTHER INFORMATION: human alpha subunit of voltage-gated potassium
      channel Kv10.1
<220> FEATURE:
<221> NAME/KEY: CDS
<222> LOCATION: (151)..(1788)
<223> OTHER INFORMATION: Kv10.1

<400> SEQUENCE: 1

| | | | | | |
|---|---|---|---|---|---|
| ggcaatgtct | gagccctag | ctgtgctggt | ccgggctggc | ctctctaaga | cagtgcaggc | 60 |
| cacgtgatcc | atcctcctag | aggcagtgag | caggtgaggg | accctacca | cagccaggag | 120 |
| gaaaaagcta | ggcgtccact | ttccgcagcc | atgctcaaac | agagtgagag | gagacggtcc | 180 |
| tggagctaca | ggcctggaa | cacgacggag | aatgagggca | gccaacaccg | caggagcatt | 240 |
| tgctccctgg | gtgcccgttc | cggctcccag | gccagcatcc | acggctggac | agagggcaac | 300 |
| tataactact | acatcgagga | agacgaagac | ggggaggagg | aggaccagtg | aaggacgac | 360 |
| ctggcagaag | aggaccagca | ggcaggggag | gtcaccaccg | ccaagcccga | gggccccagc | 420 |
| gaccctccgg | ccctgctgtc | cacgctgaat | gtgaacgtgg | gtggcacag | ctaccagctg | 480 |
| gactactgcg | agctggccgg | cttccccaag | acgcgcctag | gtcgcctggc | cacctccacc | 540 |
| agccgcagcc | gccagctaag | cctgtgcgac | gactacgagg | agcagacaga | cgaatacttc | 600 |
| ttcgaccgcg | acccggccgt | cttccagctg | gtctacaatt | tctacctgtc | cggggtgctg | 660 |
| ctggtgctcg | acgggctgtg | tccgcgccgc | ttcctggagg | agctgggcta | ctggggcgtg | 720 |
| cggctcaagt | acacgccacg | ctgctgccgc | atctgcttcg | aggagcggcg | cgacgagctg | 780 |
| agcgaacggc | tcaagatcca | gcacgagctg | cgcgcgcagg | cgcaggtcga | ggaggcggag | 840 |
| gaactcttcc | gcgacatgcg | cttctacggc | ccgcagcggc | gccgcctctg | gaacctcatg | 900 |
| gagaagccat | tctcctcggt | ggccgccaag | gccatcgggg | tggcgtccag | caccttcgtg | 960 |
| ctcgtctccg | tggtggcgct | ggcgctcaac | accgtggagg | agatgcagca | gcactcgggg | 1020 |
| cagggcgagg | gcggcccaga | cctgcggccc | atcctggagc | acgtggagat | gctgtgcatg | 1080 |
| ggcttcttca | cgctcgagta | cctgctgcgc | ctagcctcca | cgcccgacct | gaggcgcttc | 1140 |
| gcgcgcagcg | ccctcaacct | ggtggacctg | gtggccatcc | tgccgctcta | ccttcagctg | 1200 |
| ctgctcgagt | gcttcacggg | cgagggccac | caacgcggcc | agacggtggg | cagcgtgggt | 1260 |
| aaggtgggtc | aggtgttgcg | cgtcatgcgc | ctcatgcgca | tcttccgcat | cctcaagctg | 1320 |
| gcgcgccact | ccaccggact | gcgtgccttc | ggcttcacgg | tgcgccagtg | ctaccagcag | 1380 |
| gtgggctgcc | tgctgctctt | catcgccatg | gcatcttca | ctttctctgc | ggctgtctac | 1440 |
| tctgtggagc | acgatgtgcc | cagcaccaac | ttcactacca | tccccactc | ctggtggtgg | 1500 |
| gccgcggtga | gcatctccac | cgtgggctac | ggagacatgt | acccagagac | ccacctgggc | 1560 |
| aggtttttg | ccttcctctg | cattgctttt | ggatcattc | tcaacgggat | gcccatttcc | 1620 |
| atcctctaca | caagttttc | tgattactac | agcaagctga | aggcttatga | gtataccacc | 1680 |
| atacgcaggg | agaggggaga | ggtgaacttc | atgcagagag | ccagaaagaa | gatagctgag | 1740 |
| tgtttgcttg | gaagcaaccc | acagctcacc | ccaagacaag | agaattagta | ttttatagga | 1800 |

-continued

```
catgtggctg gtagattcca tgaacttcaa ggcttcattg ctcttttttt aatcattatg    1860
attggcagca aaaggaaatg tgaagcagac atacacaaag gccatttcgt tcacaaagta    1920
ctgcctctag aaatactcat tttggcccaa actcagaatg tctcatagtt gctctgtgtt    1980
gtgtgaaaca tctgaccttc tcaatgacgt tgatattgaa aacctgaggg gagcaacagc    2040
ttagattttt cttgtagctt ctcgtggcat ctagctaata aatattttt ggacttgaaa     2100 aaa                                                                  2103
```

<210> SEQ ID NO 2
<211> LENGTH: 1638
<212> TYPE: DNA
<213> ORGANISM: Homo sapiens
<220> FEATURE:
<223> OTHER INFORMATION: human alpha subunit of voltage-gated potassium
      channel Kv10.1 coding sequence
<220> FEATURE:
<221> NAME/KEY: CDS
<222> LOCATION: (1)..(1638)
<223> OTHER INFORMATION: Kv10.1

<400> SEQUENCE: 2

```
atg ctc aaa cag agt gag agg aga cgg tcc tgg agc tac agg ccc tgg       48
Met Leu Lys Gln Ser Glu Arg Arg Arg Ser Trp Ser Tyr Arg Pro Trp
 1               5                  10                  15 aac acg acg gag aat gag ggc agc caa cac cgc agg agc att tgc tcc       96
Asn Thr Thr Glu Asn Glu Gly Ser Gln His Arg Arg Ser Ile Cys Ser
            20                  25                  30 ctg ggt gcc cgt tcc ggc tcc cag gcc agc atc cac ggc tgg aca gag      144
Leu Gly Ala Arg Ser Gly Ser Gln Ala Ser Ile His Gly Trp Thr Glu
        35                  40                  45 ggc aac tat aac tac tac atc gag gaa gac gaa gac ggg gag gag gag      192
Gly Asn Tyr Asn Tyr Tyr Ile Glu Glu Asp Glu Asp Gly Glu Glu Glu
    50                  55                  60 gac cag tgg aag gac gac ctg gca gaa gag gac cag cag gca ggg gag      240
Asp Gln Trp Lys Asp Asp Leu Ala Glu Glu Asp Gln Gln Ala Gly Glu
65                  70                  75                  80 gtc acc acc gcc aag ccc gag ggc ccc agc gac cct ccg gcc ctg ctg      288
Val Thr Thr Ala Lys Pro Glu Gly Pro Ser Asp Pro Pro Ala Leu Leu
                85                  90                  95 tcc acg ctg aat gtg aac gtg ggt ggc cac agc tac cag ctg gac tac      336
Ser Thr Leu Asn Val Asn Val Gly Gly His Ser Tyr Gln Leu Asp Tyr
            100                 105                 110 tgc gag ctg gcc ggc ttc ccc aag acg cgc cta ggt cgc ctg gcc acc      384
Cys Glu Leu Ala Gly Phe Pro Lys Thr Arg Leu Gly Arg Leu Ala Thr
        115                 120                 125 tcc acc agc cgc agc cgc cag cta agc ctg tgc gac gac tac gag gag      432
Ser Thr Ser Arg Ser Arg Gln Leu Ser Leu Cys Asp Asp Tyr Glu Glu
    130                 135                 140 cag aca gac gaa tac ttc ttc gac cgc gac ccg gcc gtc ttc cag ctg      480
Gln Thr Asp Glu Tyr Phe Phe Asp Arg Asp Pro Ala Val Phe Gln Leu
145                 150                 155                 160 gtc tac aat ttc tac ctg tcc ggg gtg ctg ctg gtg ctc gac ggg ctg      528
Val Tyr Asn Phe Tyr Leu Ser Gly Val Leu Leu Val Leu Asp Gly Leu
                165                 170                 175 tgt ccg cgc cgc ttc ctg gag gag ctg ggc tac tgg ggc gtg cgg ctc      576
Cys Pro Arg Arg Phe Leu Glu Glu Leu Gly Tyr Trp Gly Val Arg Leu
            180                 185                 190 aag tac acg cca cgc tgc tgc cgc atc tgc ttc gag gag cgg cgc gac      624
Lys Tyr Thr Pro Arg Cys Cys Arg Ile Cys Phe Glu Glu Arg Arg Asp
        195                 200                 205
```

```
gag ctg agc gaa cgg ctc aag atc cag cac gag ctg cgc gcg cag gcg    672
Glu Leu Ser Glu Arg Leu Lys Ile Gln His Glu Leu Arg Ala Gln Ala
    210                 215                 220 cag gtc gag gag gcg gag gaa ctc ttc cgc gac atg cgc ttc tac ggc    720
Gln Val Glu Glu Ala Glu Glu Leu Phe Arg Asp Met Arg Phe Tyr Gly
225                 230                 235                 240 ccg cag cgg cgc cgc ctc tgg aac ctc atg gag aag cca ttc tcc tcg    768
Pro Gln Arg Arg Arg Leu Trp Asn Leu Met Glu Lys Pro Phe Ser Ser
                245                 250                 255 gtg gcc gcc aag gcc atc ggg gtg gcg tcc agc acc ttc gtg ctc gtc    816
Val Ala Ala Lys Ala Ile Gly Val Ala Ser Ser Thr Phe Val Leu Val
            260                 265                 270 tcc gtg gtg gcg ctg gcg ctc aac acc gtg gag gag atg cag cag cac    864
Ser Val Val Ala Leu Ala Leu Asn Thr Val Glu Glu Met Gln Gln His
        275                 280                 285 tcg ggg cag ggc gag ggc ggc cca gac ctg cgg ccc atc ctg gag cac    912
Ser Gly Gln Gly Glu Gly Gly Pro Asp Leu Arg Pro Ile Leu Glu His
    290                 295                 300 gtg gag atg ctg tgc atg ggc ttc ttc acg ctc gag tac ctg ctg cgc    960
Val Glu Met Leu Cys Met Gly Phe Phe Thr Leu Glu Tyr Leu Leu Arg
305                 310                 315                 320 cta gcc tcc acg ccc gac ctg agg cgc ttc gcg cgc agc gcc ctc aac   1008
Leu Ala Ser Thr Pro Asp Leu Arg Arg Phe Ala Arg Ser Ala Leu Asn
                325                 330                 335 ctg gtg gac ctg gtg gcc atc ctg ccg ctc tac ctt cag ctg ctg ctc   1056
Leu Val Asp Leu Val Ala Ile Leu Pro Leu Tyr Leu Gln Leu Leu Leu
            340                 345                 350 gag tgc ttc acg ggc gag ggc cac caa cgc ggc cag acg gtg ggc agc   1104
Glu Cys Phe Thr Gly Glu Gly His Gln Arg Gly Gln Thr Val Gly Ser
        355                 360                 365 gtg ggt aag gtg ggt cag gtg ttg cgc gtc atg cgc ctc atg cgc atc   1152
Val Gly Lys Val Gly Gln Val Leu Arg Val Met Arg Leu Met Arg Ile
    370                 375                 380 ttc cgc atc ctc aag ctg gcg cgc cac tcc acc gga ctg cgt gcc ttc   1200
Phe Arg Ile Leu Lys Leu Ala Arg His Ser Thr Gly Leu Arg Ala Phe
385                 390                 395                 400 ggc ttc acg ctg cgc cag tgc tac cag cag gtg ggc tgc ctg ctg ctc   1248
Gly Phe Thr Leu Arg Gln Cys Tyr Gln Gln Val Gly Cys Leu Leu Leu
                405                 410                 415 ttc atc gcc atg ggc atc ttc act ttc tct gcg gct gtc tac tct gtg   1296
Phe Ile Ala Met Gly Ile Phe Thr Phe Ser Ala Ala Val Tyr Ser Val
            420                 425                 430 gag cac gat gtg ccc agc acc aac ttc act acc atc ccc cac tcc tgg   1344
Glu His Asp Val Pro Ser Thr Asn Phe Thr Thr Ile Pro His Ser Trp
        435                 440                 445 tgg tgg gcc gcg gtg agc atc tcc acc gtg ggc tac gga gac atg tac   1392
Trp Trp Ala Ala Val Ser Ile Ser Thr Val Gly Tyr Gly Asp Met Tyr
    450                 455                 460 cca gag acc cac ctg ggc agg ttt ttt gcc ttc ctc tgc att gct ttt   1440
Pro Glu Thr His Leu Gly Arg Phe Phe Ala Phe Leu Cys Ile Ala Phe
465                 470                 475                 480 ggg atc att ctc aac ggg atg ccc att tcc atc ctc tac aac aag ttt   1488
Gly Ile Ile Leu Asn Gly Met Pro Ile Ser Ile Leu Tyr Asn Lys Phe
                485                 490                 495 tct gat tac tac agc aag ctg aag gct tat gag tat acc acc ata cgc   1536
Ser Asp Tyr Tyr Ser Lys Leu Lys Ala Tyr Glu Tyr Thr Thr Ile Arg
            500                 505                 510 agg gag agg gga gag gtg aac ttc atg cag aga gcc aga aag aag ata   1584
Arg Glu Arg Gly Glu Val Asn Phe Met Gln Arg Ala Arg Lys Lys Ile
        515                 520                 525
```

-continued

```
gct gag tgt ttg ctt gga agc aac cca cag ctc acc cca aga caa gag     1632
Ala Glu Cys Leu Leu Gly Ser Asn Pro Gln Leu Thr Pro Arg Gln Glu
    530                 535                 540 aat tag                                                              1638
Asn
545
```

<210> SEQ ID NO 3
<211> LENGTH: 545
<212> TYPE: PRT
<213> ORGANISM: Homo sapiens
<220> FEATURE:
<223> OTHER INFORMATION: human alpha subunit of voltage-gated potassium channel Kv10.1
<220> FEATURE:
<221> NAME/KEY: PEPTIDE
<222> LOCATION: (102)..(514)
<223> OTHER INFORMATION: conserved region of voltage-gated potassium channel Kv10.1

<400> SEQUENCE: 3

```
Met Leu Lys Gln Ser Glu Arg Arg Ser Trp Ser Tyr Arg Pro Trp
  1               5                  10                  15

Asn Thr Thr Glu Asn Glu Gly Ser Gln His Arg Arg Ser Ile Cys Ser
                 20                  25                  30

Leu Gly Ala Arg Ser Gly Ser Gln Ala Ser Ile His Gly Trp Thr Glu
             35                  40                  45

Gly Asn Tyr Asn Tyr Tyr Ile Glu Glu Asp Glu Asp Gly Glu Glu
         50                  55                  60

Asp Gln Trp Lys Asp Asp Leu Ala Glu Glu Asp Gln Gln Ala Gly Glu
 65                  70                  75                  80

Val Thr Thr Ala Lys Pro Glu Gly Pro Ser Asp Pro Pro Ala Leu Leu
                 85                  90                  95

Ser Thr Leu Asn Val Asn Val Gly Gly His Ser Tyr Gln Leu Asp Tyr
                100                 105                 110

Cys Glu Leu Ala Gly Phe Pro Lys Thr Arg Leu Gly Arg Leu Ala Thr
            115                 120                 125

Ser Thr Ser Arg Ser Arg Gln Leu Ser Leu Cys Asp Asp Tyr Glu Glu
        130                 135                 140

Gln Thr Asp Glu Tyr Phe Phe Asp Arg Asp Pro Ala Val Phe Gln Leu
145                 150                 155                 160

Val Tyr Asn Phe Tyr Leu Ser Gly Val Leu Val Leu Asp Gly Leu
                165                 170                 175

Cys Pro Arg Arg Phe Leu Glu Glu Leu Gly Tyr Trp Gly Val Arg Leu
            180                 185                 190

Lys Tyr Thr Pro Arg Cys Cys Arg Ile Cys Phe Glu Glu Arg Arg Asp
        195                 200                 205

Glu Leu Ser Glu Arg Leu Lys Ile Gln His Glu Leu Arg Ala Gln Ala
    210                 215                 220

Gln Val Glu Glu Ala Glu Leu Phe Arg Asp Met Arg Phe Tyr Gly
225                 230                 235                 240

Pro Gln Arg Arg Arg Leu Trp Asn Leu Met Glu Lys Pro Phe Ser Ser
                245                 250                 255

Val Ala Ala Lys Ala Ile Gly Val Ala Ser Ser Thr Phe Val Leu Val
            260                 265                 270

Ser Val Val Ala Leu Ala Leu Asn Thr Val Glu Glu Met Gln Gln His
        275                 280                 285
```

-continued

```
Ser Gly Gln Gly Glu Gly Pro Asp Leu Arg Pro Ile Leu Glu His
    290                 295                 300

Val Glu Met Leu Cys Met Gly Phe Phe Thr Leu Glu Tyr Leu Leu Arg
305                 310                 315                 320

Leu Ala Ser Thr Pro Asp Leu Arg Arg Phe Ala Arg Ser Ala Leu Asn
                325                 330                 335

Leu Val Asp Leu Val Ala Ile Leu Pro Leu Tyr Leu Gln Leu Leu Leu
            340                 345                 350

Glu Cys Phe Thr Gly Glu Gly His Gln Arg Gly Gln Thr Val Gly Ser
        355                 360                 365

Val Gly Lys Val Gly Gln Val Leu Arg Val Met Arg Leu Met Arg Ile
    370                 375                 380

Phe Arg Ile Leu Lys Leu Ala Arg His Ser Thr Gly Leu Arg Ala Phe
385                 390                 395                 400

Gly Phe Thr Leu Arg Gln Cys Tyr Gln Gln Val Gly Cys Leu Leu Leu
                405                 410                 415

Phe Ile Ala Met Gly Ile Phe Thr Phe Ser Ala Ala Val Tyr Ser Val
            420                 425                 430

Glu His Asp Val Pro Ser Thr Asn Phe Thr Thr Ile Pro His Ser Trp
        435                 440                 445

Trp Trp Ala Ala Val Ser Ile Ser Thr Val Gly Tyr Gly Asp Met Tyr
    450                 455                 460

Pro Glu Thr His Leu Gly Arg Phe Phe Ala Phe Leu Cys Ile Ala Phe
465                 470                 475                 480

Gly Ile Ile Leu Asn Gly Met Pro Ile Ser Ile Leu Tyr Asn Lys Phe
                485                 490                 495

Ser Asp Tyr Tyr Ser Lys Leu Lys Ala Tyr Glu Tyr Thr Thr Ile Arg
            500                 505                 510

Arg Glu Arg Gly Glu Val Asn Phe Met Gln Arg Ala Arg Lys Lys Ile
        515                 520                 525

Ala Glu Cys Leu Leu Gly Ser Asn Pro Gln Leu Thr Pro Arg Gln Glu
    530                 535                 540

Asn
545

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:sense
      Oligo 1

<400> SEQUENCE: 4
gccatgctca aacagagtga gaggagac                                       28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:antisense
      Oligo 2

<400> SEQUENCE: 5
gagcgtgaag aagcccatgc acag                                           24

<210> SEQ ID NO 6
```

```
<211> LENGTH: 23
<212> TYPE: DNA
<213> ORGANISM: Artificial Sequence
<220> FEATURE:
<223> OTHER INFORMATION: Description of Artificial Sequence:RACE PCR
      gene-specific antisense Oligo 3

<400> SEQUENCE: 6
gcagcacccc ggacaggtag aaa                                         23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:nested
      gene-specific antisense Oligo 4

<400> SEQUENCE: 7
cggccgggtc gcggtcgaag aagt                                        24

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:standard 3'
      RACE PCR nested Oligo 5

<400> SEQUENCE: 8
ccaccatgag ggcagccaac accgcaggag ca                               32

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:new 3' RACE
      gene-specific sense Oligo 6

<400> SEQUENCE: 9
ggctgtctac tctgtggagc acgat                                       25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:antisense
      Oligo 7

<400> SEQUENCE: 10
gagtatttct agaggcagta ctttgtg                                     27

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:coding
      region Oligo 8

<400> SEQUENCE: 11
attctcttgt cttggggtga gctg                                        24

<210> SEQ ID NO 12
<211> LENGTH: 854
```

<212> TYPE: PRT
<213> ORGANISM: Homo sapiens
<220> FEATURE:
<223> OTHER INFORMATION: human voltage-gated potassium channel Kv2.1

<400> SEQUENCE: 12

```
Met Thr Lys His Gly Ser Arg Ser Thr Ser Ser Leu Pro Pro Glu Pro
  1               5                  10                  15

Met Glu Ile Val Arg Ser Lys Ala Cys Ser Arg Arg Val Arg Leu Asn
             20                  25                  30

Val Gly Gly Leu Ala His Glu Val Leu Trp Arg Thr Leu Asp Arg Leu
         35                  40                  45

Pro Arg Thr Arg Leu Gly Lys Leu Arg Asp Cys Asn Thr His Asp Ser
 50                  55                  60

Leu Leu Glu Val Cys Asp Asp Tyr Ser Leu Asp Asp Asn Glu Tyr Phe
 65                  70                  75                  80

Phe Asp Arg His Pro Gly Ala Phe Thr Ser Ile Leu Asn Phe Tyr Arg
                 85                  90                  95

Thr Gly Arg Leu His Met Met Glu Glu Met Cys Ala Leu Ser Phe Ser
                100                 105                 110

Gln Glu Leu Asp Tyr Trp Gly Ile Asp Glu Ile Tyr Leu Glu Ser Cys
            115                 120                 125

Cys Gln Ala Arg Tyr His Gln Lys Lys Glu Gln Met Asn Glu Glu Leu
130                 135                 140

Lys Arg Glu Ala Glu Thr Leu Arg Glu Arg Glu Gly Glu Glu Phe Asp
145                 150                 155                 160

Asn Thr Cys Cys Ala Glu Lys Arg Lys Lys Leu Trp Asp Leu Leu Glu
                165                 170                 175

Lys Pro Asn Ser Ser Val Ala Ala Lys Ile Leu Ala Ile Ile Ser Ile
                180                 185                 190

Met Phe Ile Val Leu Ser Thr Ile Ala Leu Ser Leu Asn Thr Leu Pro
            195                 200                 205

Glu Leu Gln Ser Leu Asp Glu Phe Gly Gln Ser Thr Asp Asn Pro Gln
210                 215                 220

Leu Ala His Val Glu Ala Val Cys Ile Ala Trp Phe Thr Met Glu Tyr
225                 230                 235                 240

Leu Leu Arg Phe Leu Ser Ser Pro Lys Lys Trp Lys Phe Phe Lys Gly
                245                 250                 255

Pro Leu Asn Ala Ile Asp Leu Leu Ala Ile Leu Pro Tyr Tyr Val Thr
                260                 265                 270

Ile Phe Leu Thr Glu Ser Asn Lys Ser Val Leu Gln Phe Gln Asn Val
            275                 280                 285

Arg Arg Val Val Gln Ile Phe Arg Ile Met Arg Ile Leu Arg Ile Leu
290                 295                 300

Lys Leu Ala Arg His Ser Thr Gly Leu Gln Ser Leu Gly Phe Thr Leu
305                 310                 315                 320

Arg Arg Ser Tyr Asn Glu Leu Gly Leu Leu Ile Leu Phe Leu Ala Met
                325                 330                 335

Gly Ile Met Ile Phe Ser Ser Leu Val Phe Phe Ala Glu Lys Asp Glu
                340                 345                 350

Asp Asp Thr Lys Phe Lys Ser Ile Pro Ala Ser Phe Trp Trp Ala Thr
            355                 360                 365

Ile Thr Met Thr Thr Val Gly Tyr Gly Asp Ile Tyr Pro Lys Thr Leu
370                 375                 380
```

-continued

```
Leu Gly Lys Ile Val Gly Gly Leu Cys Cys Ile Ala Gly Val Leu Val
385                 390                 395                 400

Ile Ala Leu Pro Ile Pro Ile Val Asn Asn Phe Ser Glu Phe Tyr
            405                 410                 415

Lys Glu Gln Lys Arg Gln Glu Lys Ala Ile Lys Arg Arg Glu Ala Leu
                420                 425                 430

Glu Arg Ala Lys Arg Asn Gly Ser Ile Val Ser Met Asn Met Lys Asp
            435                 440                 445

Ala Phe Ala Arg Ser Ile Glu Met Met Asp Ile Val Val Glu Lys Asn
450                 455                 460

Gly Glu Asn Met Gly Lys Lys Asp Lys Val Gln Asp Asn His Leu Ser
465                 470                 475                 480

Pro Asn Lys Trp Lys Trp Thr Lys Arg Thr Leu Ser Glu Thr Ser Ser
                485                 490                 495

Ser Lys Ser Phe Glu Thr Lys Glu Gln Gly Ser Pro Glu Lys Ala Arg
            500                 505                 510

Ser Ser Ser Ser Pro Gln His Leu Asn Val Gln Gln Leu Glu Asp Met
            515                 520                 525

Tyr Asn Lys Met Ala Lys Thr Gln Ser Gln Pro Ile Leu Asn Thr Lys
530                 535                 540

Glu Ser Ala Ala Gln Ser Lys Pro Lys Glu Glu Leu Glu Met Glu Ser
545                 550                 555                 560

Ile Pro Ser Pro Val Ala Pro Leu Pro Thr Arg Thr Glu Gly Val Ile
                565                 570                 575

Asp Met Arg Ser Met Ser Ser Ile Asp Ser Phe Ile Ser Cys Ala Thr
            580                 585                 590

Asp Phe Pro Glu Ala Thr Arg Phe Ser His Ser Pro Leu Thr Ser Leu
            595                 600                 605

Pro Ser Lys Thr Gly Gly Ser Thr Ala Pro Glu Val Gly Trp Arg Gly
            610                 615                 620

Ala Leu Gly Ala Ser Gly Gly Arg Phe Val Glu Ala Asn Pro Ser Pro
625                 630                 635                 640

Asp Ala Ser Gln His Ser Ser Phe Phe Ile Glu Ser Pro Lys Ser Ser
                645                 650                 655

Met Lys Thr Asn Asn Pro Leu Lys Leu Arg Ala Leu Lys Val Asn Phe
            660                 665                 670

Met Glu Gly Asp Pro Ser Pro Leu Leu Pro Val Leu Gly Met Tyr His
            675                 680                 685

Asp Pro Leu Arg Asn Arg Gly Ser Ala Ala Ala Val Ala Gly Leu
            690                 695                 700

Glu Cys Ala Thr Leu Leu Asp Lys Ala Val Leu Ser Pro Glu Ser Ser
705                 710                 715                 720

Ile Tyr Thr Thr Ala Ser Ala Lys Thr Pro Pro Arg Ser Pro Glu Lys
                725                 730                 735

His Thr Ala Ile Ala Phe Asn Phe Glu Ala Gly Val His Gln Tyr Ile
            740                 745                 750

Asp Ala Asp Thr Asp Asp Glu Gly Gln Leu Leu Tyr Ser Val Asp Ser
            755                 760                 765

Ser Pro Pro Lys Ser Leu Pro Gly Ser Thr Ser Pro Lys Phe Ser Thr
            770                 775                 780

Gly Thr Arg Ser Glu Lys Asn His Phe Glu Ser Ser Pro Leu Pro Thr
785                 790                 795                 800

Ser Pro Lys Phe Leu Arg Gln Asn Cys Ile Tyr Ser Thr Glu Ala Leu
```

```
            805                 810                 815
Thr Gly Lys Gly Pro Ser Gly Gln Glu Lys Cys Lys Leu Glu Asn His
            820                 825                 830

Ile Ser Pro Asp Val Arg Val Leu Pro Gly Gly Ala His Gly Ser
            835                 840                 845

Thr Arg Asp Gln Ser Ile
            850

<210> SEQ ID NO 13
<211> LENGTH: 806
<212> TYPE: PRT
<213> ORGANISM: Homo sapiens
<220> FEATURE:
<223> OTHER INFORMATION: human voltage-gated potassium channel Kv2.2

<400> SEQUENCE: 13

Met Ala Glu Lys Ala Pro Pro Gly Leu Asn Arg Lys Thr Ser Arg Ser
  1               5                  10                  15

Thr Leu Ser Leu Pro Pro Glu Pro Val Asp Ile Ile Arg Ser Lys Thr
                 20                  25                  30

Cys Ser Arg Arg Val Lys Ile Asn Val Gly Gly Leu Asn His Glu Val
             35                  40                  45

Leu Trp Arg Thr Leu Asp Arg Leu Pro Arg Thr Arg Leu Gly Lys Leu
         50                  55                  60

Arg Asp Cys Asn Thr His Glu Ser Leu Glu Val Cys Asp Asp Tyr
 65                  70                  75                  80

Asn Leu Asn Glu Asn Glu Tyr Phe Phe Asp Arg His Pro Gly Ala Phe
                 85                  90                  95

Thr Ser Ile Leu Asn Phe Tyr Arg Thr Gly Lys Leu His Met Met Glu
            100                 105                 110

Glu Met Cys Ala Leu Ser Phe Gly Gln Glu Leu Asp Tyr Trp Gly Ile
        115                 120                 125

Asp Glu Ile Tyr Leu Glu Ser Cys Cys Gln Ala Arg Tyr His Gln Lys
    130                 135                 140

Lys Glu Gln Met Asn Glu Glu Leu Arg Arg Glu Ala Glu Thr Met Arg
145                 150                 155                 160

Asp Gly Glu Gly Glu Phe Asp Asn Thr Cys Cys Pro Asp Lys Arg
                165                 170                 175

Lys Lys Leu Trp Asp Leu Leu Glu Lys Pro Asn Ser Ser Val Ala Ala
            180                 185                 190

Lys Ile Leu Ala Ile Val Ser Ile Leu Phe Ile Val Leu Ser Thr Ile
        195                 200                 205

Ala Leu Ser Leu Asn Thr Leu Pro Glu Leu Gln Glu Thr Asp Glu Phe
    210                 215                 220

Gly Gln Leu Asn Asp Asn Arg Gln Leu Ala His Val Glu Ala Val Cys
225                 230                 235                 240

Ile Ala Trp Phe Thr Met Glu Tyr Leu Leu Arg Phe Leu Ser Ser Pro
                245                 250                 255

Asn Lys Trp Lys Phe Phe Lys Gly Pro Leu Asn Val Ile Asp Leu Leu
            260                 265                 270

Ala Ile Leu Pro Tyr Tyr Val Thr Ile Phe Leu Thr Glu Ser Asn Lys
        275                 280                 285

Ser Val Leu Gln Phe Gln Asn Val Arg Arg Val Val Gln Ile Phe Arg
    290                 295                 300

Ile Met Arg Ile Leu Arg Ile Leu Lys Leu Ala Arg His Ser Thr Gly
```

-continued

```
305                 310                 315                 320

Leu Gln Ser Leu Gly Phe Thr Leu Arg Arg Ser Tyr Asn Glu Leu Gly
                325                 330                 335

Leu Leu Ile Leu Phe Leu Ala Met Gly Ile Met Ile Phe Ser Ser Leu
                340                 345                 350

Val Phe Phe Ala Glu Lys Asp Glu Asp Ala Thr Lys Phe Thr Ser Ile
                355                 360                 365

Pro Ala Ser Phe Trp Trp Ala Thr Ile Thr Met Thr Thr Val Gly Tyr
370                 375                 380

Gly Asp Ile Tyr Pro Lys Thr Leu Leu Gly Lys Ile Val Gly Gly Leu
385                 390                 395                 400

Cys Cys Ile Ala Gly Val Leu Val Ile Ala Leu Pro Ile Pro Ile Ile
                405                 410                 415

Val Asn Asn Phe Ser Glu Phe Tyr Lys Glu Gln Lys Arg Gln Glu Lys
                420                 425                 430

Ala Ile Lys Arg Arg Glu Ala Leu Glu Arg Ala Lys Arg Asn Gly Ser
                435                 440                 445

Ile Val Ser Met Asn Leu Lys Asp Ala Phe Ala Arg Ser Met Glu Leu
                450                 455                 460

Ile Asp Val Ala Val Glu Lys Ala Gly Glu Ser Ala Asn Thr Lys Asp
465                 470                 475                 480

Ser Ala Asp Asn His Leu Ser Pro Ser Arg Trp Lys Trp Ala Arg
                485                 490                 495

Lys Ala Leu Ser Glu Thr Ser Ser Asn Lys Ser Phe Glu Asn Lys Tyr
                500                 505                 510

Gln Glu Val Ser Gln Lys Asp Ser His Glu Gln Leu Asn Asn Thr Phe
                515                 520                 525

Ser Ser Ser Pro Gln His Leu Ser Ala Gln Lys Leu Glu Met Leu Tyr
530                 535                 540

Asn Glu Ile Thr Lys Thr Gln Pro His Ser His Pro Asn Pro Asp Cys
545                 550                 555                 560

Gln Glu Lys Pro Glu Arg Pro Ser Ala Tyr Glu Glu Ile Glu Met
                565                 570                 575

Glu Glu Val Val Cys Pro Gln Glu Gln Leu Ala Val Ala Gln Thr Glu
                580                 585                 590

Val Ile Val Asp Met Lys Ser Thr Ser Ser Ile Asp Ser Phe Thr Ser
                595                 600                 605

Cys Ala Thr Asp Phe Thr Glu Thr Glu Arg Ser Pro Leu Pro Pro Pro
                610                 615                 620

Ser Ala Ser His Leu Gln Met Lys Phe Pro Thr Asp Leu Pro Gly Thr
625                 630                 635                 640

Glu Glu His Gln Arg Ala Arg Gly Pro Pro Phe Leu Thr Leu Ser Arg
                645                 650                 655

Glu Lys Gly Pro Ala Ala Arg Asp Gly Thr Leu Glu Tyr Ala Pro Val
                660                 665                 670

Asp Ile Thr Val Asn Leu Asp Ala Ser Gly Ser Gln Cys Gly Leu His
                675                 680                 685

Ser Pro Leu Gln Ser Asp Asn Ala Thr Asp Ser Pro Lys Ser Ser Leu
                690                 695                 700

Lys Gly Ser Asn Pro Leu Lys Ser Arg Ser Leu Lys Val Asn Phe Lys
705                 710                 715                 720

Glu Asn Arg Gly Ser Ala Pro Gln Thr Pro Pro Ser Thr Ala Arg Pro
                725                 730                 735
```

```
Leu Pro Val Thr Thr Ala Asp Phe Ser Leu Thr Thr Pro Gln His Ile
            740                 745                 750

Ser Thr Ile Leu Leu Glu Glu Thr Pro Ser Gln Gly Asp Arg Pro Cys
        755                 760                 765

Trp Ala Leu Arg Phe Gln Arg Leu Val Arg Asp Leu Pro Lys Gly Cys
    770                 775                 780

Pro Pro Gly Phe Pro Ser Arg Asn Cys Ser Leu Ser Leu Gln Glu Arg
785                 790                 795                 800

Gly Gly Ala Ser Leu Lys
                805
```

```
<210> SEQ ID NO 14
<211> LENGTH: 26
<212> TYPE: PRT
<213> ORGANISM: Homo sapiens
<220> FEATURE:
<221> NAME/KEY: DOMAIN
<222> LOCATION: (1)..(26)
<223> OTHER INFORMATION: S6 domain of voltage-gated potassium channel
      Kv10.1

<400> SEQUENCE: 14

Phe Phe Ala Phe Leu Cys Ile Ala Phe Gly Ile Ile Leu Asn Gly Met
  1               5                  10                  15

Pro Ile Ser Ile Leu Tyr Asn Lys Phe Ser
            20                  25
```

```
<210> SEQ ID NO 15
<211> LENGTH: 26
<212> TYPE: PRT
<213> ORGANISM: Homo sapiens
<220> FEATURE:
<221> NAME/KEY: DOMAIN
<222> LOCATION: (1)..(26)
<223> OTHER INFORMATION: S6 domain of voltage-gated potassium channel
      Kv6.1

<400> SEQUENCE: 15

Val Val Ala Leu Ser Ser Ile Leu Ser Gly Ile Leu Leu Met Ala Phe
  1               5                  10                  15

Pro Val Thr Ser Ile Phe His Thr Phe Ser
            20                  25
```

```
<210> SEQ ID NO 16
<211> LENGTH: 26
<212> TYPE: PRT
<213> ORGANISM: Homo sapiens
<220> FEATURE:
<221> NAME/KEY: DOMAIN
<222> LOCATION: (1)..(26)
<223> OTHER INFORMATION: S6 domain of voltage-gated potassium channel
      Kv2.1

<400> SEQUENCE: 16

Ile Val Gly Gly Leu Cys Cys Ile Ala Gly Val Leu Val Ile Ala Leu
  1               5                  10                  15

Pro Ile Pro Ile Ile Val Asn Asn Phe Ser
            20                  25
```

```
<210> SEQ ID NO 17
<211> LENGTH: 22
<212> TYPE: DNA
<213> ORGANISM: Artificial Sequence
<220> FEATURE:
```

```
<223> OTHER INFORMATION: Description of Artificial Sequence:
      Kv10.1-specific amplification primer

<400> SEQUENCE: 17
tgggctgcct gctgctcttc at                                              22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      Kv10.1-specific amplification primer

<400> SEQUENCE: 18
ctctcccctc tccctgcgta tggt                                            24
```